US012576196B2

(12) United States Patent
Guo et al.

(10) Patent No.:  US 12,576,196 B2
(45) Date of Patent:      Mar. 17, 2026

(54) MEDICAL FLUID CONTAINER ASSEMBLING SYSTEM AND METHOD

(71) Applicants: BAXTER INTERNATIONAL INC., Deerfield, IL (US); BAXTER HEALTHCARE SA, Glattpark (CH)

(72) Inventors: Zhixiong Guo, Guangzhou (CN); Zhibin Liu, Tianjin (CN)

(73) Assignees: BAXTER INTERNATIONAL INC., Deerfiled, IL (US); BAXTER HEALTHCARE SA, Glattpark (CH)

( * ) Notice: Subject to any disclaimer, the term of this patent is extended or adjusted under 35 U.S.C. 154(b) by 391 days.

(21) Appl. No.: 18/038,595

(22) PCT Filed: Nov. 18, 2021

(86) PCT No.: PCT/US2021/059800
§ 371 (c)(1),
(2) Date: May 24, 2023

(87) PCT Pub. No.: WO2022/115300
PCT Pub. Date: Jun. 2, 2022

(65) Prior Publication Data
US 2024/0001014 A1     Jan. 4, 2024

(30) Foreign Application Priority Data
Nov. 25, 2020    (CN) .......................... 202011337331.6

(51) Int. Cl.
*A61M 1/28*        (2006.01)
*A61M 1/16*        (2006.01)
(52) U.S. Cl.
CPC ....... *A61M 1/1668* (2014.02); *A61M 2207/10* (2013.01)

(58) Field of Classification Search
CPC .......... A61M 2207/00; A61M 2207/10; A61M 1/668
See application file for complete search history.

(56) References Cited

U.S. PATENT DOCUMENTS

2016/0193444 A1*  7/2016  Tomes ................ A61M 25/002
                                                                  206/571
2020/0164197 A1    5/2020  Shun et al.

FOREIGN PATENT DOCUMENTS

CN        209 649 629          11/2019
CN         209649629 U   *   11/2019
WO       WO-02/30489 A2 *   4/2002

OTHER PUBLICATIONS

International Search Report—PCT/US2021/059800 mailing date Mar. 7, 2022—3 pages.

(Continued)

*Primary Examiner* — Jeffry H Aftergut
(74) *Attorney, Agent, or Firm* — K&L Gates LLP

(57)                    ABSTRACT
A medical fluid container assembling system and method are disclosed. The system includes a coiled catheter pallet for receiving a catheter tip portion of a coiled catheter. The system also includes a coiled catheter preparation unit configured to place the coiled catheter on the coiled catheter pallet in a predetermined posture, and cause the catheter tip portion of the coiled catheter to extend a predetermined length. The system further includes a container body pallet for receiving a container tube of a container body. Additionally, the system includes a container body preparation unit configured to place the container body on the container body pallet in a predetermined posture, and cause the container tube of the container body to extend a predetermined length. The system also includes a container tube (Continued)

expander, a catheter tip gluing device, and an assembling mechanism configured to insert the catheter tip portion into the container tube.

31 Claims, 17 Drawing Sheets

(56) References Cited

OTHER PUBLICATIONS

Written Opinion—PCT/US2021/059800 mailing date Mar. 7, 2022—3 pages.

* cited by examiner

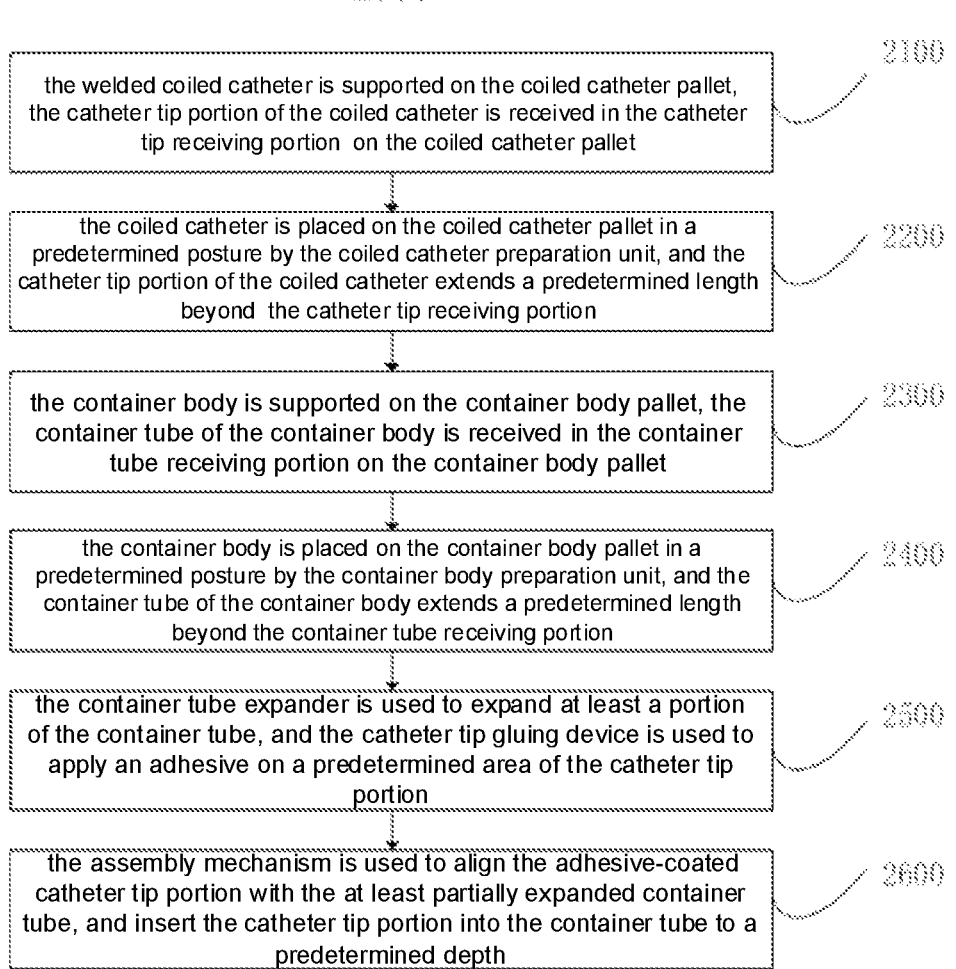

2000 the welded coiled catheter is supported on the coiled catheter pallet, the catheter tip portion of the coiled catheter is received in the catheter tip receiving portion on the coiled catheter pallet — 2100 the coiled catheter is placed on the coiled catheter pallet in a predetermined posture by the coiled catheter preparation unit, and the catheter tip portion of the coiled catheter extends a predetermined length beyond the catheter tip receiving portion — 2200 the container body is supported on the container body pallet, the container tube of the container body is received in the container tube receiving portion on the container body pallet — 2300 the container body is placed on the container body pallet in a predetermined posture by the container body preparation unit, and the container tube of the container body extends a predetermined length beyond the container tube receiving portion — 2400 the container tube expander is used to expand at least a portion of the container tube, and the catheter tip gluing device is used to apply an adhesive on a predetermined area of the catheter tip portion — 2500 the assembly mechanism is used to align the adhesive-coated catheter tip portion with the at least partially expanded container tube, and insert the catheter tip portion into the container tube to a predetermined depth — 2600

Fig.19

MEDICAL FLUID CONTAINER ASSEMBLING SYSTEM AND METHOD

CROSS REFERENCE TO RELATED APPLICATIONS

The present application is a national phase entry of PCT Patent Application No. PCT/US2021/059800, filed on Nov. 18, 2021, which claims priority to the Chinese Patent Application No. 202011337331.6, filed on Nov. 25, 2020, the entire contents of which are incorporated herein by reference.

TECHNICAL FIELD

The present disclosure generally relates to a medical fluid container assembling system and method.

BACKGROUND

Due to disease or other causes, a person's renal system may fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) may accumulate in blood and tissues.

Kidney failure and reduced kidney function can be treated with dialysis. Dialysis removes waste, toxins and excess water from the body that would otherwise have been removed by normal functioning kidneys. Dialysis treatment for replacement of kidney functions is critical to many people because the treatment is life-saving. A person with failed kidneys cannot survive without at least the filtering function that replaces the kidneys.

One type of kidney failure therapy is peritoneal dialysis (PD). In PD, a dialysis solution, also called dialysis fluid, is infused into a patient's peritoneal cavity via a catheter implanted therein. The dialysis fluid contacts the peritoneal membrane of the patient's peritoneal cavity. Waste, toxins and excess water pass from the patient's bloodstream, through the peritoneal membrane, and into the dialysis fluid due to diffusion and osmosis, i.e., an osmotic gradient occurs across the membrane. Used or spent dialysis fluid is drained from the patient's peritoneal cavity, removing waste, toxins and excess water from the patient. This cycle may be repeated multiple times.

There are various types of PD therapies, including continuous ambulatory peritoneal dialysis (CAPD), automated peritoneal dialysis (APD) and continuous flow peritoneal dialysis (CFPD). CAPD is a manual dialysis treatment, where the patient manually connects an implanted catheter to a drain device to allow used dialysis fluid to drain from the peritoneal cavity. The patient then switches fluid communication so that the patient catheter communicates with a bag of fresh dialysis fluid to infuse the fresh dialysis fluid through the catheter and into the patient. Then, the patient can disconnect the catheter from the fresh dialysis fluid bag and allow the dialysis fluid to dwell within the peritoneal cavity, wherein the transfer of waste, toxins and excess water takes place. After a dwell period, the patient repeats the above manual dialysis procedure. In CAPD, the patient is required to repeat the drain, fill and dwell cycles multiple times, for example, four times, a day.

Automated peritoneal dialysis (APD) is similar to CAPD in that its dialysis treatment also includes drain, fill and dwell cycles. However, APD machines perform the cycles automatically, typically while the patient sleeps. APD machines connect fluidly to an implanted catheter, to a bag of fresh dialysis fluid and to a fluid drain.

APD machines pump fresh dialysis fluid from a dialysis fluid source, through the catheter and into the patient's peritoneal cavity. APD machines also allow for the dialysis fluid to dwell within the cavity and for the transfer of waste, toxins and excess water from the patient's bloodstream to the dialysis fluid to take place. Then, the APD machines pumps the used dialysis fluid from the peritoneal cavity through the catheter to the drainage device. APD machines are usually computer controlled so that the dialysis treatment occurs automatically when the patient is connected to the dialysis machines (for example when the patient is sleeping). That is, the APD system automatically and sequentially pumps fluid into the peritoneal cavity, allows it to dwell therein, and pumps the fluid out of the peritoneal cavity, and then repeats the above process.

As with the manual process, several drain, fill and dwell cycles will occur during APD. A "last fill" is usually occurred at the end of the APD treatment, which remains in the patient's peritoneal cavity when the patient is disconnected from the dialysis machines during the day. APD eliminates the need for patients to manually perform the drain, fill and dwell operations.

As mentioned above, both CAPD and APD involve the use of medical fluid containers. For example, the drainage container is used to receive used dialysis fluid from the patient. The drainage container mainly includes a container body and a tube in the form of a coiled catheter. One end of the tube is connected to a container tube of the container body in a sealed manner, and the other end of the tube can be in fluid communication with the patient's peritoneal cavity to drain the used dialysis fluid into the drainage container.

An existing method for assembling a medical fluid container includes the following steps: a worker manually applies an adhesive to a catheter tip portion of the coiled catheter, then uses a tool to elastically expand a port of the container tube, and then inserts the catheter tip portion with the adhesive into the container tube, so that the tube is sealed and joined to the container tube of the container body. However, this manual operation method is inefficient, labor intensive, and costly. Therefore, there is a need in the art for an automated medical fluid container assembling system and method in order to reduce production costs and improve efficiency.

SUMMARY

A medical fluid container assembling system and method is provide. The system and method can automatically assemble the container body and coiled catheter, thereby improving the efficiency of assembly.

According to one aspect of the disclosure, a medical fluid container assembling system is provided. The system may include: at least one coiled catheter pallet for supporting a coiled catheter, the coiled catheter pallet being provided with a catheter tip receiving portion for receiving a catheter tip portion of the coiled catheter; a coiled catheter preparation unit configured to place the coiled catheter on the coiled catheter pallet in a predetermined posture, and cause the catheter tip portion of the coiled catheter to extend a predetermined length beyond the catheter tip receiving portion; at least one container body pallet for supporting a container body, the container body pallet being provided with a container tube receiving portion for receiving the container tube of the container body; a container body preparation unit configured to place the container body on the container body pallet in a predetermined posture, and cause the container tube of the container body to extend a predetermined length beyond the container tube receiving portion; a container tube expander configured to expand at least a portion of the container tube; a catheter tip gluing device configured to apply adhesive on a predetermined area of the catheter tip portion; and an assembling mechanism configured to align the catheter tip portion applied with adhesive with the at least partially expanded container tube and insert the catheter tip portion into the container tube to a predetermined depth.

According to another aspect of the disclosure, a method for assembling a medical fluid container is provided. The method may include: supporting a welded coiled catheter on a coiled catheter pallet, a catheter tip portion of the coiled catheter being received in a catheter tip portion receiving portion of the coiled catheter pallet; placing, by a coiled catheter preparation unit, the coiled catheter on the coiled catheter pallet in a predetermined posture, and causing the catheter tip portion of the coiled catheter to extend a predetermined length beyond the catheter tip portion receiving portion; supporting a container body on a container body pallet, a container tube of the container body being received in a container tube receiving portion of the container body pallet; placing, by a container body preparation unit, the container body on the container body pallet in a predetermined posture, and causing the container tube of the container body to extend a predetermined length beyond the container tube receiving portion; expanding, by a container tube expander, at least a portion of the container tube; applying, by a catheter tip gluing device, adhesive on a predetermined area of the catheter tip portion; and aligning, by an assembling mechanism, the catheter tip portion applied with adhesive with the at least partially expanded container tube, and inserting the catheter tip portion into the container tube to a predetermined depth.

In the medical fluid container assembling system and method of the present disclosure, the coiled catheter and the container body are placed, positioned, and adjusted in parallel by an automated device, the expansion of the container tube and the glue on the catheter tip are realized simultaneously, and then the automatic assembling mechanism inserts the catheter tip into the container tube to a predetermined depth, thereby realizing the automatic assembling of the medical fluid container, improving the assembling efficiency, and reducing the labor intensity of the workers.

The above is an overview of the disclosure, and details may be simplified, summarized and omitted. Those skilled in the art should realize that this part is only illustrative and is not intended to limit the scope of the disclosure in any way. This summary is neither intended to determine the key features or essential features of the claimed subject matter, nor is it intended to be used as an auxiliary means to determine the scope of the claimed subject matter.

BRIEF DESCRIPTION OF THE DRAWINGS

Through the following detailed description in conjunction with the accompanying drawings and the appended claims, those skilled in the art will more fully understand the above and other features of the content of this application. It can be understood that these drawings and detailed description only depict several exemplary embodiments of the content of the present application, and should not be considered as limiting the scope of the content of the present application. By referring to the drawings, the content of this disclosure will be explained more clearly and in detail.

FIG. 14B illustrates a schematic perspective view of the container body adjusting mechanism 450 adjusting a container tube 12a;

FIG. 16 illustrates a side sectional view of the container tube expander 500 of FIG. 15, wherein an expansion head 520 is inserted into the container tube 12a;

FIG. 19 illustrates a flow chart of a method for assembling a medical fluid container 2000 according to an embodiment.

Figure 1:
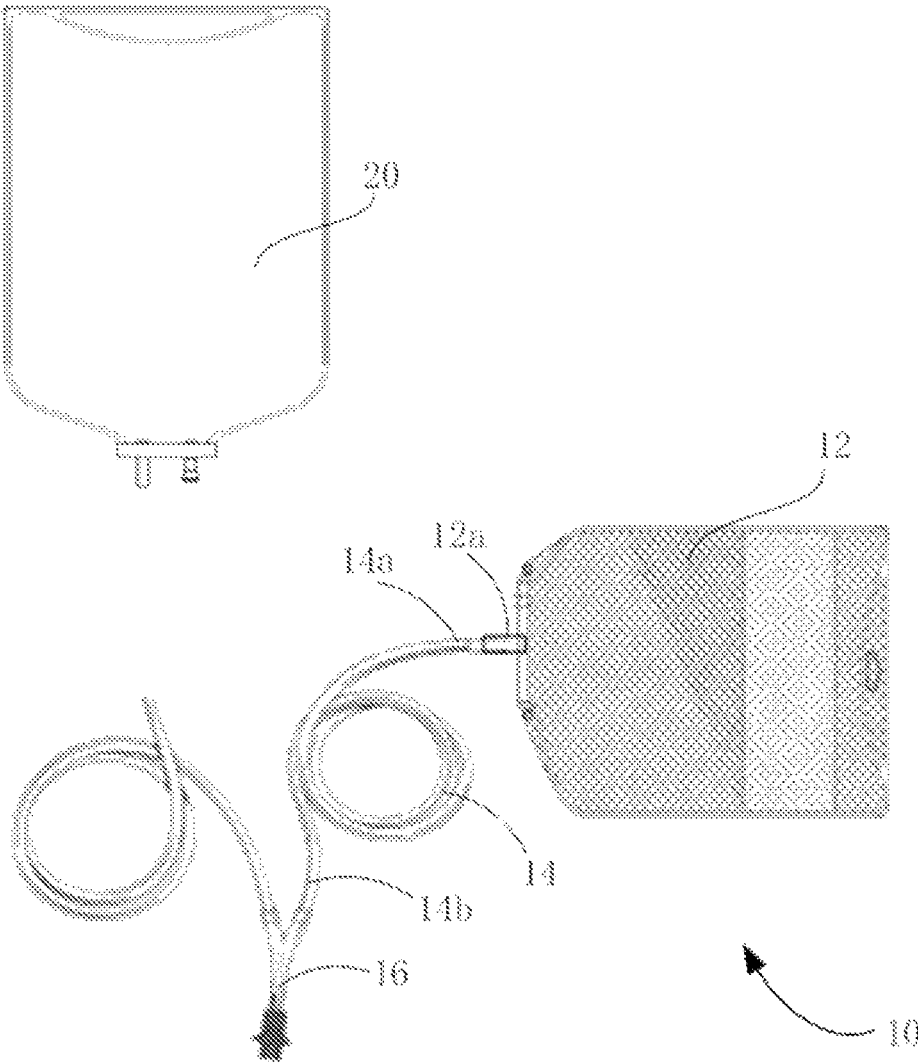
FIG. 1 illustrates a schematic structural diagram of an exemplary medical fluid container 10.

LIST OF REFERENCE NUMBERS 10 medical fluid container
12 container body
12a container tube
14 coiled catheter 14*a*, 14*b* catheter tip portion
16 Y-shaped catheter tip
20 dialysate container
1000 medical fluid container assembling system
100, 100' coiled catheter pallet
110, 110' catheter tip receiving portion
111, 112, 114 protrusion
116 tool access groove
120 coiled catheter synchronous belt
130, 130' sidewall gap
210 coiled catheter gripping mechanism
212 first gripper
214 second gripper
220 coiled catheter detector
222, 224 laser sensor
226 guide rod
230 buffer belt
232 buffer clamp
240 coiled catheter pre-adjusting mechanism
242 length sensor
244 adjusting clamp
250 coiled catheter transferring mechanism
252 triaxial mechanical arm
260 coiled catheter adjusting mechanism
262 coiled catheter vertical positioning device
264 coiled catheter push plate
266 catheter tip sensor
300 container body pallet
310 container tube receiving portion
320 container body synchronous belt
410 feeding belt
412 visual detector
414, 416 light source
420 container body gripper
422 sucker
424 container body indenter
430 container body positioning device
432 plate
434 container body positioning block
436 positioning bump
440 container tube clamp
450 container body adjusting mechanism
452 container body vertical positioning device
454 container body push plate
500 container tube expander
510 container tube indenter
520 expansion head
600 catheter tip gluing device
610 first adhesive container
614 scale
620 second adhesive container
612, 622 outlet port
710 catheter tip clamp
2000 method for assembling a medical fluid container

DETAILED DESCRIPTION

In the following detailed description, reference is made to the drawings constituting a part of the specification. In the drawings, unless the context dictates otherwise, similar reference numbers usually indicate similar components. The illustrative embodiments described in the detailed description, drawings, and claims are not meant to be limiting. Without departing from the spirit or scope of the subject matter of the present application, other implementation modes and other changes may be adopted. It should be understood that various aspects of the content of the application described generally in the application and illustrated in the drawings can be configured, replaced, combined, and designed with various different configurations, and all of these clearly constitute a part of the contents of the disclosure.

The following will take a drainage container used in peritoneal dialysis therapy as an example to describe a system and method for assembling a medical fluid container. However, a person skilled in the art would appreciate that the system and method described in this disclosure are also applicable to assemble other types of medical fluid containers with a catheter.

Figure 4A:
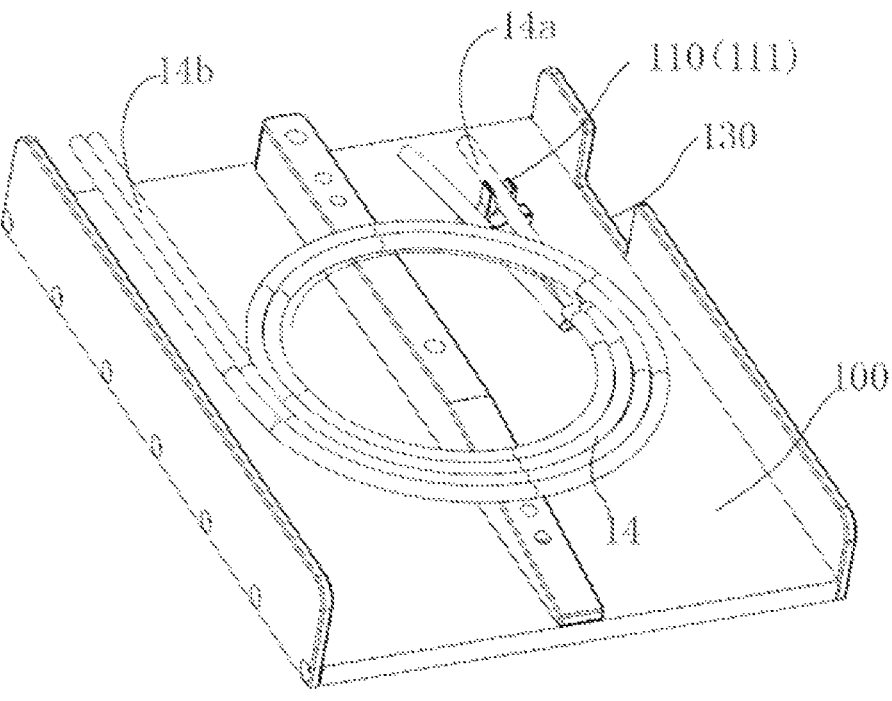
FIG. 4A illustrates a schematic perspective view of a coiled catheter pallet 100 according to an embodiment.

Referring to FIG. 1, a medical fluid container 10 is illustrated. As shown in FIG. 1, the medical fluid container 10 includes a flexible container body 12 and a coiled catheter 14 (having been disassembled into two parts). In an example, the container body 12 is connected to the coiled catheter 14 via a container tube 12*a* in a sealed manner, and may be used to contain used dialysis fluid. The coiled catheter 14 before disassembly is typically formed by coiling two parallel flexible catheters into loops, and then being fixed by spot welding at multiple locations to maintain the coiled state of the coiled catheter 14 (as shown in FIG. 4A). Referring to FIG. 1, a catheter tip portion 14*a* of one catheter of the disassembled coiled catheter 14 is connected to the container tube 12*a* of the container body 12 in a sealed manner, the other catheter tip portion 14*b* of the catheter is connected to the Y-shaped catheter tip 16. One end of the other catheter of the disassembled coiled catheter 14 is connected to a dialysate container 20 containing the dialysis fluid, and the other end is connected to the Y-shaped catheter tip 16. The outer diameter of the catheter tip portion 14*a* may be equal to or slightly smaller than the inner diameter of the container tube 12*a*. After the container tube 12*a* is expanded, the catheter tip portion 14*a* is inserted into the container tube 12*a* and is connected to the container tube 12*a* by adhesive in a sealed manner.

The catheter implanted in the peritoneal cavity of the patient can be optionally in fluid communication with the dialysate container 20 or the medical fluid container 10 through the Y-shaped catheter tip 16, so as to infuse the dialysis fluid from the dialysate container 20 into the patient's body, or drain the waste fluid from the patient's body to the container body 12.

The medical fluid container assembling system and method will be described in detail below with reference to the accompanying drawings according to embodiments of the present disclosure.

Figure 2:
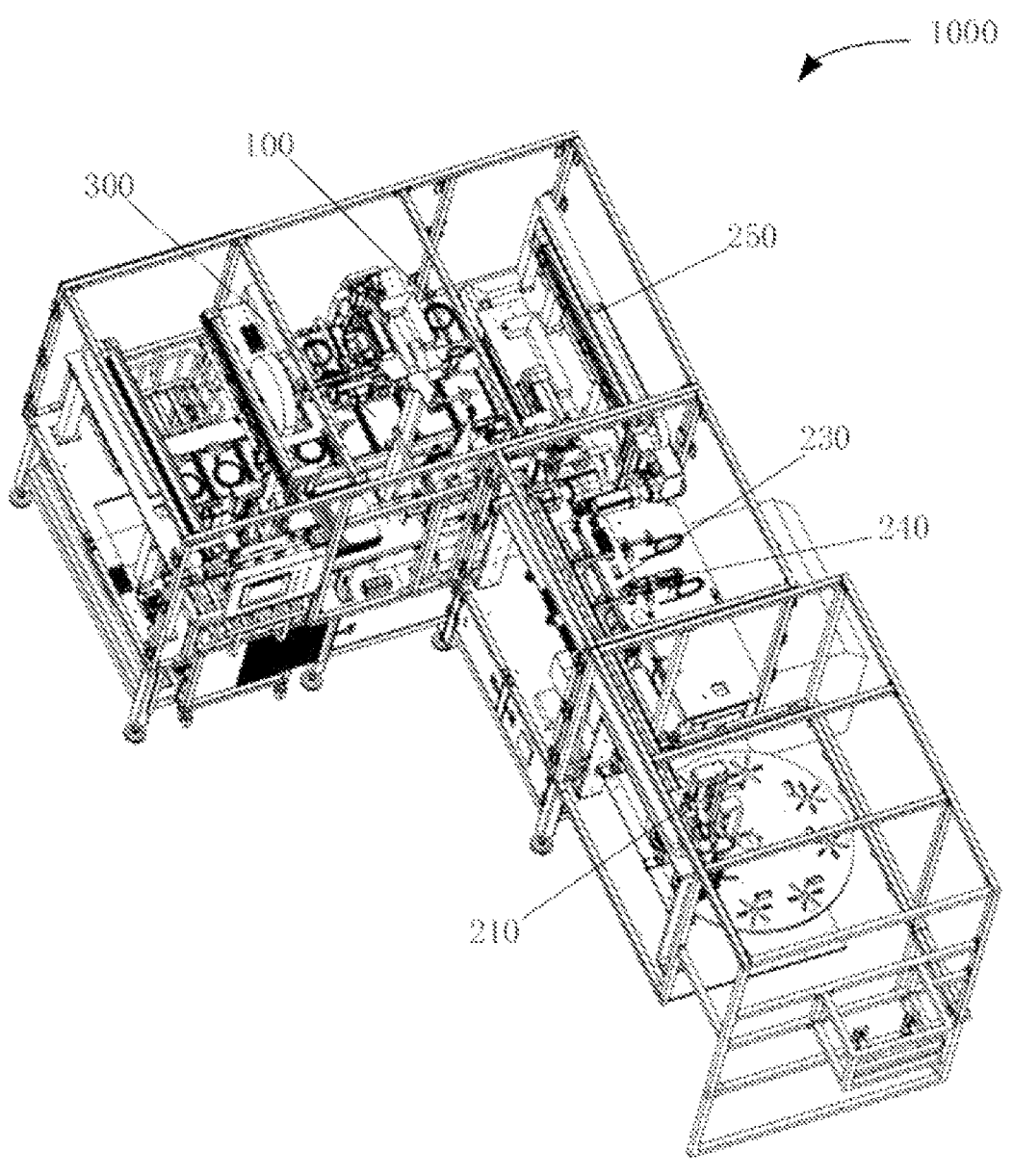
FIG. 2 illustrates a perspective view of a medical fluid container assembling system 1000 according to an embodiment of the present disclosure.
Figure 3:
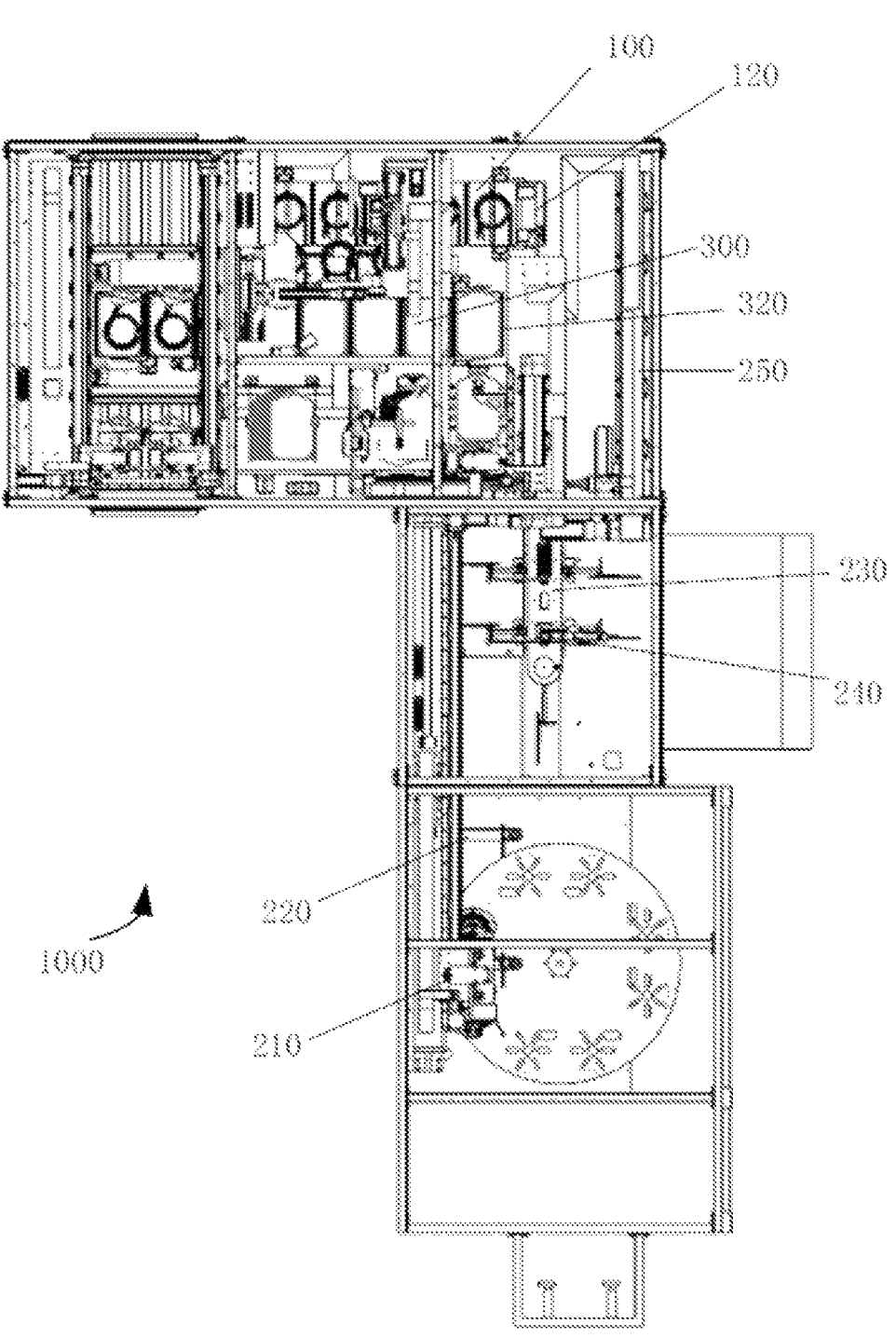
FIG. 3 illustrates a top view of the medical fluid container assembling system 1000 of FIG. 2.

FIGS. 2-3 exemplarily illustrate a structure of a medical fluid container assembling system 1000 according to an embodiment of the present disclosure. Specifically, FIG. 2 illustrates a perspective view of the medical fluid container assembling system 1000, and FIG. 3 illustrates a top view of the medical fluid container assembling system 1000 of FIG. 2.

As shown in FIGS. 2-3, the medical fluid container assembling system 1000 includes at least one coiled catheter pallet 100, and each coiled catheter pallet 100 may support a coiled catheter 14. Further referring to FIG. 4A, the coiled catheter pallet 100 is provided with a catheter tip receiving portion 110 for receiving a catheter tip portion 14*a* portion of the coiled catheter 14. In the illustrated embodiment, the catheter tip receiving portion 110 is placed close to an edge on one side of the coiled catheter pallet 100 (i.e., the right side in FIG. 4A). When the catheter tip portion 14*a* of the coiled catheter 14 is received in the catheter tip receiving portion 110, the catheter tip portion 14*b* is placed close to an edge on another side of the coiled catheter pallet 100 (i.e., the left side in FIG. 4A), so that the coiled catheter 14 is properly positioned on the coiled catheter pallet 100. As shown in FIG. 4A, the catheter tip receiving portion 110 may include a protrusion 111 on which a groove is provided, preferably a groove with a semicircular bottom. The width of the groove is configured to be equal to or slightly larger than the outer diameter of the catheter tip portion 14a, such that the catheter tip portion 14a can be received in the groove.

Figure 4B:
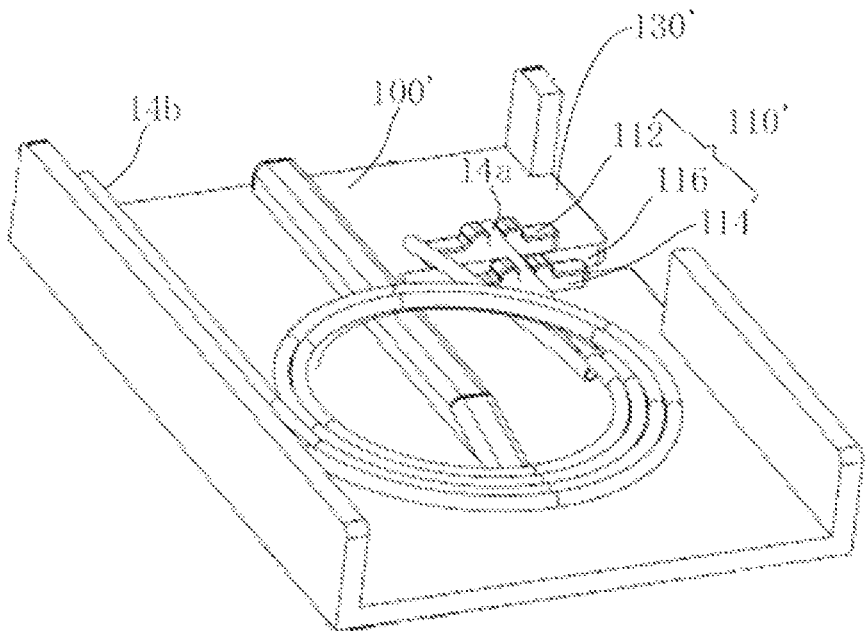
FIG. 4B illustrates a schematic perspective view of a coiled catheter pallet 100' according to another embodiment.

A person skilled in the art would appreciate that the catheter tip receiving portion 110 is not limited to the specific configuration shown in FIG. 4A, and may also be implemented in other suitable forms. For example, as shown in FIG. 4B, a catheter tip receiving portion 110' may include two parallel and spaced protrusions 112 and 114, and each of the protrusions 112, 114 is provided with a groove, preferably a groove with a semicircular bottom. The width of the groove is configured to be equal to or slightly larger than the outer diameter of the catheter tip portion 14a, so that the catheter tip portion 14a can be received in the groove. In some embodiments, a tool access groove 116 may be further provided between the two protrusions 112 and 114. The tool access groove 116 extends from the edge of the coiled catheter pallet 100' and at least over the grooves of the protrusions 112 and 114, such that a catheter tip clamp 710 (referring to FIG. 15 or FIG. 18) can easily extend into the tool access grove 116 to clamp the catheter tip portion 14a.

In some embodiments, as shown in FIG. 4A and FIG. 4B, a side wall of the coiled catheter pallet 100, 100' close to the catheter tip receiving portion 110, 110' may be provided with a side wall notch 130, 130' to avoid interference between the side wall and mechanical components used in subsequent assembly. For example, the side wall notch 130, 130' can prevent the catheter tip clamp 710 (referring to FIG. 15 or FIG. 18) from being obstructed during its movement for clamping the catheter tip portion 14a.

Referring to FIGS. 2-3, in some embodiments, the medical fluid container assembling system 1000 may include a plurality of coiled catheter pallets 100, and correspondingly, a coiled catheter synchronous belt 120 is provided for conveying these coiled catheter pallets 100. In the illustrated embodiments, the coiled catheter synchronous belt 120 is configured as a circular belt, on which a plurality of coiled catheter pallets 100 can be carried. The coiled catheter synchronous belt 120 can be driven (for example, by a stepping motor) to move the coiled catheter pallets 100 toward a catheter tip gluing device 600 (referring to FIG. 15).

In some embodiments, the medical fluid container assembling system 1000 may further include a coiled catheter preparation unit. The coiled catheter preparation unit is used for placing, adjusting and positioning the coiled catheter 14 before the container body 12 and the coiled catheter 14 are assembled, so that the coiled catheter 14 is placed on the coiled catheter pallets 100 in a predetermined posture. In the predetermined posture, the catheter tip portion 14a protrudes a predetermined length from the catheter tip receiving portion 110 (for example, from the outside of the protrusion 111 in FIG. 4A, or from the outside of the protrusion 112 in FIG. 4B), so as to facilitate the assembly with the container tube 12a of the container body 12.

Figure 5:
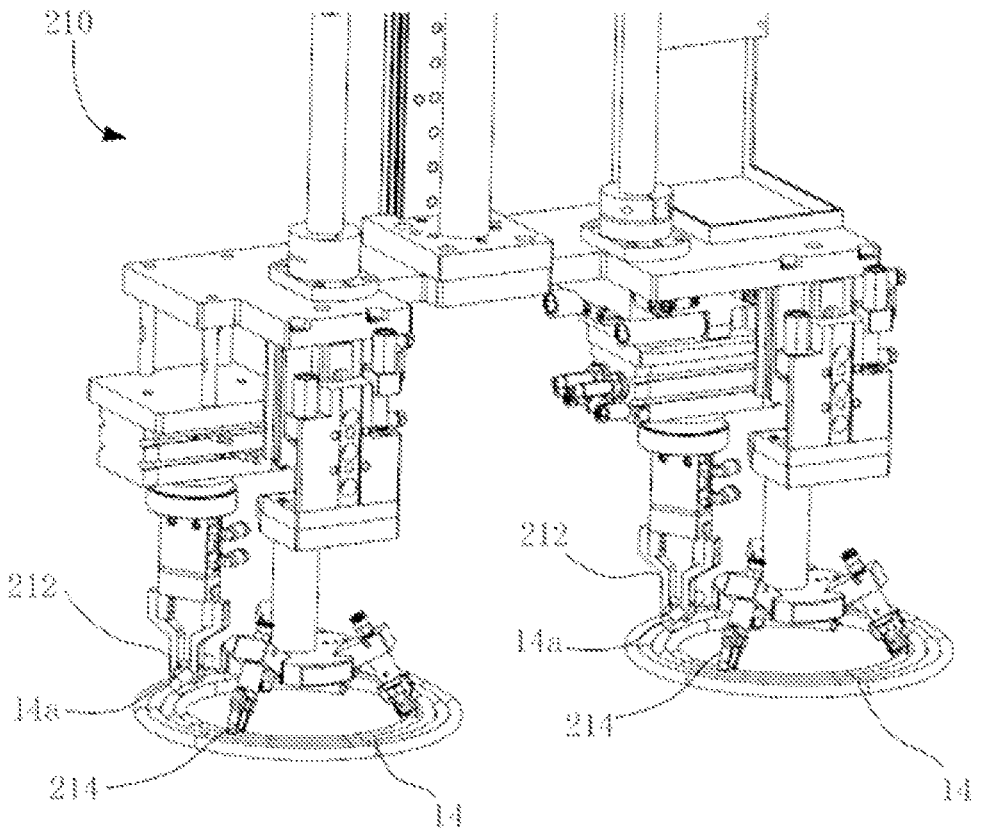
FIG. 5 illustrates a schematic perspective view of a coiled catheter gripping mechanism 210 according to an embodiment.

In some embodiments, the coiled catheter preparation unit includes a coiled catheter gripping mechanism 210 for gripping the coiled catheter 14 welded in a previous process at the coiled catheter feeding station, and transferring it to the coiled catheter pallet 100. Referring to FIG. 5, the coiled catheter gripping mechanism 210 includes a first gripper 212 for gripping the catheter tip portion 14a of the coiled catheter 14 and at least three (for example, 3, 4 and 5) second grippers 214 for gripping an inner circumference of the coiled catheter 14. The gripping portions of all second grippers 214 are arranged in the same horizontal plan, so that the gripped coiled catheter 14 can be oriented in the horizontal direction. Preferably, the gripping positions of the second grippers 214 of the coiled gripping mechanism 210 on the inner circle of the coiled catheter 14 are evenly distributed along the circumferential direction.

In the embodiment shown in FIG. 5, the coiled catheter gripping mechanism 210 includes two sets of first grippers 212 and second grippers 214, wherein the first gripper 212 and the second gripper 214 of each set cooperate with each other. However, the present disclosure is not limited thereto. In some embodiments, the coiled catheter gripping mechanism 210 may only include one set of first gripper and second gripper for gripping the coiled catheter 14. Alternatively, in some embodiments, the coiled catheter gripping mechanism 210 may include more than two sets of first gripper and second gripper, for example, three sets, four sets and the like, for gripping multiple coiled catheters 14 at the same time.

In actual production, the coiled catheter 14 may be twisted or poorly welded. It is necessary to identify and discard the coiled catheters with these defects as soon as possible to reduce the scrap rate of the final product. In order to inspect the welding quality of the coiled catheter 14, the operator may perform a visual inspection during the process of moving the coiled catheter 14 by the coiled catheter gripping mechanism 210 to determine the welding quality of the coiled catheter 14.

Figure 6:
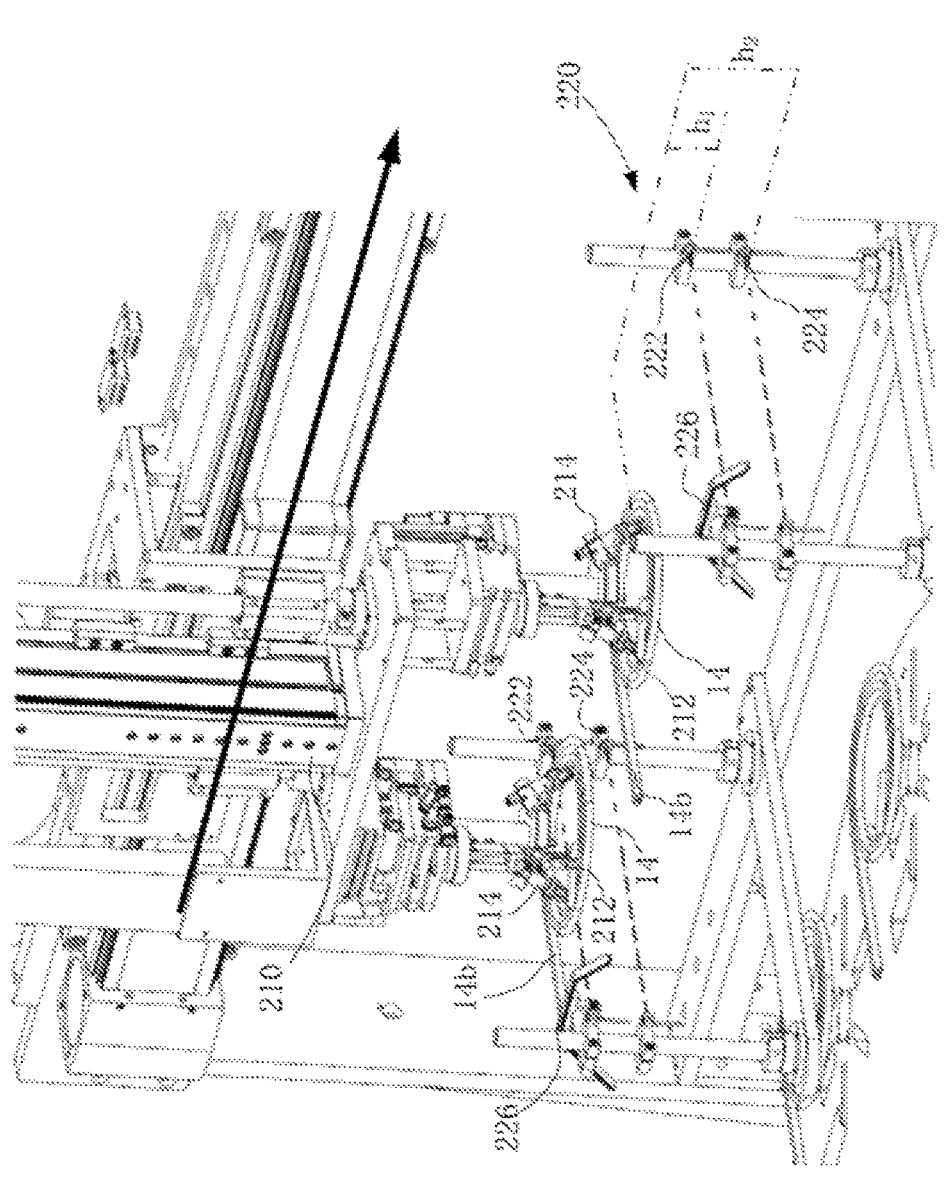
FIG. 6 illustrates a schematic perspective view of a coiled catheter detector 220 according to an embodiment.

In some embodiments, the coiled catheter preparation unit further includes a coiled catheter detector 220 for automatically detecting the quality of the coiled catheter. FIG. 6 illustrates a coiled catheter detector 220. As shown in FIG. 6, the coiled catheter detector 220 is placed in a conveying path of the coiled catheter 14 (in the direction of the arrow in FIG. 6), and the coiled catheter gripping mechanism 210 can make each of the two gripped coiled catheters 14 pass by a corresponding coiled catheter detector 220 in a horizontal posture. Specifically, the coiled catheter gripping mechanism 210 grips two coiled catheters 14 and then raises them to a starting position of the conveying path. At this starting position (e.g., the left side in FIG. 6), each of the two gripped coiled catheters 14 is located on the left side of its corresponding coiled catheter detector 220. As the coiled catheter gripping mechanism 210 moves along the conveying path in the direction indicated by the arrow in FIG. 6 (i.e., the direction to the right side in FIG. 6), the gripped coiled catheter 14 on the left passes through the coiled catheter detector 220 on the left for detection, and the gripped coil catheter 14 on the right passes through the coiled catheter detector 220 on the right for detection. The coiled catheter detector 220 is configured to detect whether the height of the coiled catheter 14 passing through it in the vertical direction (that is, the projected height of the coiled catheter in the vertical direction) exceeds a predetermined range. If the height of the coiled catheter 14 in the vertical direction exceeds a certain value, it can be determined that the coiled catheter 14 is poorly welded.

In the embodiments shown in FIG. 6, the coiled catheter detector 220 optionally includes two laser sensors 222 and 224 that are separated by a certain distance in the vertical direction. The laser sensor 222 is disposed at a height lower than the plane where the gripping portion of the second grippers 214 is located by a distance $h_1$ and is used to detect whether a twist degree of the coiled catheter 14 exceeds an allowable range. The laser sensor 224 is disposed at a height that is lower than the plane where the gripping portion of the second gripper 214 is located by a distance $h_2$ and is used to detect whether the coiled catheter 14 is poorly welded.

When being spot-welded, the coiled catheter 14 may be twisted to a certain extent, and various parts of the coiled catheter 14 are not in the same plane. If the twist exceeds a certain degree, when the coiled catheter 14 passes the laser sensor 222, a part of the catheter body will block the laser beam emitted by the laser sensor 222, so that the laser sensor 222 can generate a first detection signal to indicate that the coiled catheter 14 is twisted. Otherwise, the twist degree of the coiled catheter 14 is within an acceptable range. It could be appreciated that the distance $h_1$ is related to the allowable twist degree, and can be appropriately set according to the requirements of the product quality standard. For example, the distance $h_1$ may ranges 20-25 mm. It could be appreciated that when the coiled catheter is not severely twisted in actual production, the laser sensor 222 can be omitted.

If there is false welding on the coiled catheter 14, a part of the catheter body of the coiled catheter 14 may be separated from the rest catheter body and sag under the action of gravity. If the sag distance of the catheter body of the coiled catheter 14 exceeds a certain range, the coiled catheter 14 is considered to be poorly welded and should be discard. When the poorly welded coiled catheter 14 passes the laser sensor 224, the sagging part of the catheter body will block the laser beam emitted by the laser sensor 224, so that the laser sensor 224 generates a second detection signal to indicate that the coiled catheter 14 is poorly welded. Otherwise, the coiled catheter 14 is not poorly welded. It could be appreciated that the distance $h_2$ is related to an allowable degree of poor welding, and can be appropriately set according to the requirements of the product quality standard. For example, the distance $h_2$ may ranges 70-100 mm.

In the illustrated embodiment, the catheter tip portion 14*b* of the coiled catheter 14 to be connected to the Y-shaped catheter tip 16 is not welded to the rest parts of the coiled catheter 14, and will sag under the action of gravity, thereby interfering the laser sensors detectors 222, 224. In some embodiments, in order to prevent the quality inspection of the coiled catheter from being interfered by the catheter tip portion 14*b* of the coiled catheter 14, the coiled catheter detectors 220 can also be provided with a horizontal guide rod 226, as shown in FIG. 6. The guide rod 226 extends substantially along the moving direction of the coiled catheter 14, and the height of the guide rod 226 is lower than the height of the plane where the gripping portion of the second gripper 214 is located, but higher than the height of the laser 222. When the coiled catheter gripping mechanism 210 passes the gripped coiled catheter 14 through the coiled catheter detector 220, the guide rod 226 can support and guide the catheter tip portion 14*b* of the coiled catheter 14 to prevent the catheter tip portion 14*b* from sagging and a false detection caused by the sagging catheter tip portion 14*b*.

In some cases, a welding spot between the outermost part (that is, the catheter tip portion of the coiled catheter 14 to be connected to the Y-shaped catheter tip 16) and the adjacent inner part (hereinafter, referred to as "outer welding spot") of the coiled catheter 14 may also be poorly welded, and the outermost part may detach from the rest part under the action of gravity to sag. In the presence of the guide rod

226, the catheter tip portion 14*b* of the coiled catheter 14 is supported by the guide rod 226 and will not sag and be detected by the laser 222.

In this case, in order to detect the welding quality of the outer welding spot of the coiled catheter 14, the coiled catheter detector 220 may optionally include a distance measuring sensor. The distance measuring sensor can be disposed on the coiled catheter gripping mechanism 210 at a position aligned with the outermost tube of the gripped coiled catheter 14. The distance measuring sensor can emit a detection beam (such as laser beam, infrared light beam) downward in the vertical direction. In the case where the outer welding spots of the coiled catheter 14 are poorly welded while the rest catheters of the coiled catheter 14 are well welded, the main part of the coiled catheter 14 is roughly on the same horizontal plane, while the outermost tube sags relative to the main part. In this case, the distance measuring sensor can be used to detect whether a distance between the outermost tube and the distance measuring sensor exceeds a distance from the horizontal plane where the coiled catheter 14 is located to the distance measuring sensor (equal to a difference between the height of the distance measuring sensor and the height of the plane of the gripping portion of the gripper 214). If the distance measuring sensor detects that the distance to the outermost tube of the coiled catheter 14 is greater than the distance to the horizontal plane where the coiled catheter 14 is located, it can be determined that the outer welding spot is poorly welded.

When a welding defect is detected on a coiled catheter 14 by manual visual inspection or by the coiled catheter detector 220, the relevant coiled catheter 14 may be scrapped. In some embodiments, a special coiled catheter waste box may be provided for collecting scrapped coiled catheters 14. The coiled catheter waste box may be disposed downstream of the coiled catheter detector 220, preferably below the end point of the conveying path indicated by the arrow in FIG. 6, and therefore, the coiled catheter gripping mechanism 210 can directly release the first gripper 212 and the second gripper 214 when passing over the coiled catheter waste box, so that the scrapped coiled catheter falls into the coiled catheter waste box for subsequent processing.

In some embodiments, the coiled catheter preparation unit may further include a buffer belt 230 for buffering and moving a plurality of coiled catheters 14. As shown in FIGS. 2-3, the buffer belt 230 is configured as a circular belt, which is disposed downstream of the coiled catheter detector 220. The coiled catheter gripping mechanism 210 can grip the coiled catheter 14 from the coiled catheter feeding station, and transfer the coiled catheter 14 to the buffer belt 230 after the coiled catheter 14 passes the test of the coiled catheter detector 220. The buffer belt 230 can receive a plurality of coiled catheters 14 and transfer the coiled catheters 14 placed thereon toward the coiled catheter pallet 100.

Figure 7:
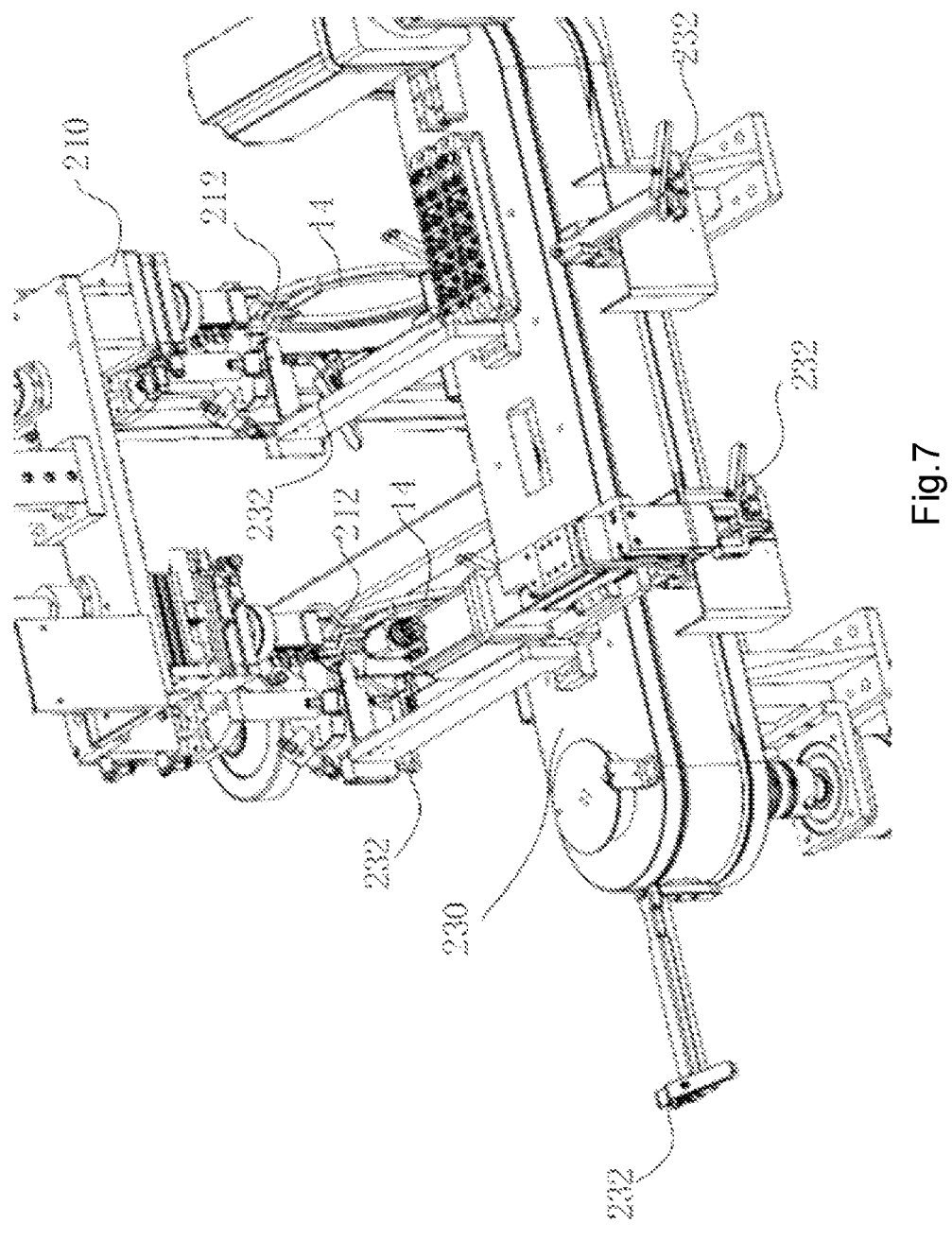
FIG. 7 illustrates a schematic perspective view of a buffer belt 230 according to an embodiment.

Referring to FIG. 7, in some embodiments, after the coiled catheter gripping mechanism 210 passes the gripped coiled catheter 14 through the coiled catheter detector 220 to complete the welding inspection, the second gripper 214 gripping the coiled catheter 14 is released, and only the first gripper 212 grips the catheter tip portion 14*a* of the coiled catheter 14, so that the coiled catheter 14 is turned from a horizontal orientation to a vertical orientation. The buffer belt 230 is provided with a plurality of buffer clamps 232. When the coiled catheter gripping mechanism 210 moves the catheter tip portion 14*a* to a position aligned with the buffer clamp 232, the buffer clamp 232 clamps the catheter tip portion 14*a*, and then the first gripper 212 is opened to release the catheter tip portion 14a. At this time, the coiled catheter 14 is only clamped by the buffer clamp 232, and the coiled catheter 14 is thus transferred to the buffer belt 230.

In some cases, after the coiled catheters 14 are transferred to the buffer belt 230, the length of the catheter tip portions 14a extending beyond the buffer clamps 232 may be inconsistent, thereby affecting subsequent processing. To this end, in some embodiments, the buffer tape 230 is optionally provided with a coiled catheter pre-adjusting mechanism 240 for adjusting the length of the catheter tip portion 14a extending beyond the buffer clamp 232.

Figure 8:
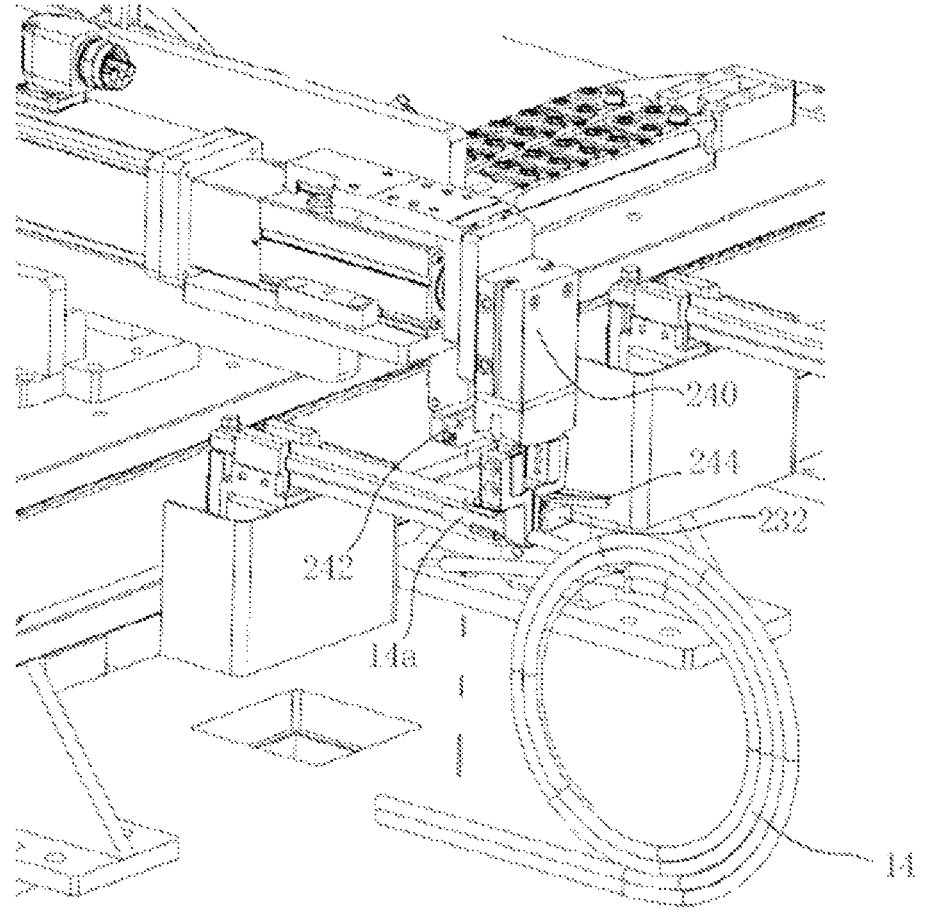
FIG. 8 illustrates a schematic perspective view of a coiled catheter pre-adjusting mechanism 240 according to an embodiment.

As shown in FIG. 8, the coiled catheter pre-adjusting mechanism 240 is placed in the movement path of the buffer clamp 232. The coiled catheter pre-adjusting mechanism 240 includes a length sensor 242 and an adjusting clamp 244. The adjusting clamp 244 can clamp the catheter tip portion 14a and be driven to move the catheter tip portion 14a toward or away from the length sensor 242. When the buffer clamp 232 clamping the catheter tip portion 14a moves to a position aligned with the adjusting clamp 244, the adjusting clamp 244 is driven to clamp the catheter tip portion 14a. Then, the buffer clamp 232 is released, and the catheter tip portion 14a is driven to move toward or away from the length sensor 242. When detecting an end edge of the catheter tip portion 14a, the length sensor 242 sends a control signal to stop the adjusting clamp 244, and then the buffer clamp 232 clamps the catheter tip portion 14a again and the adjusting clamp 244 is opened. At this time, the length of the catheter tip portion 14a extending beyond the buffer clamp 232 is adjusted to a predetermined length, and the pre-adjusting operation is completed. Then, the buffer belt 230 continues to transfer the pre-adjusted coiled catheter 14 toward the coiled catheter pallet 100.

Figure 9:
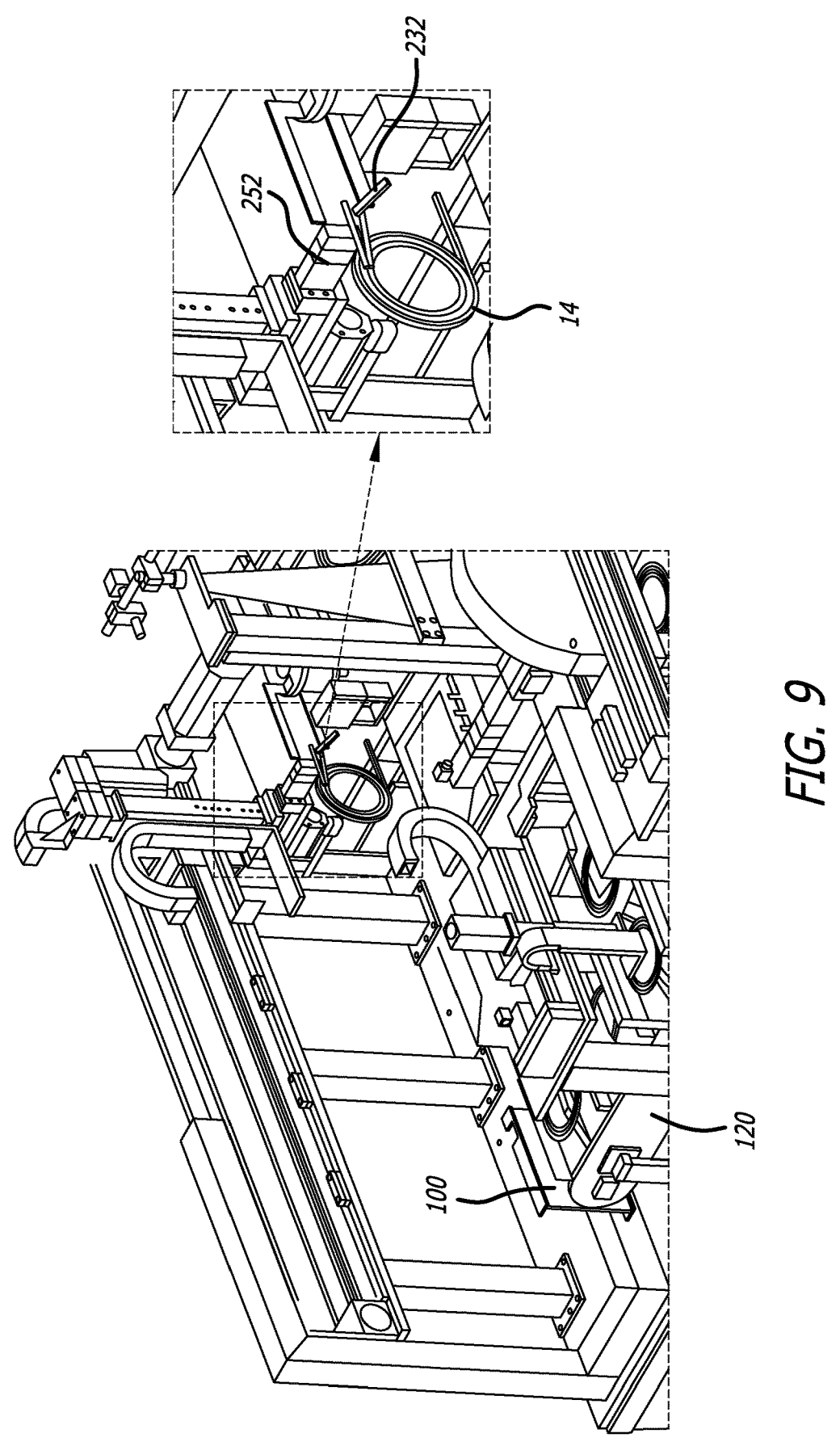
FIG. 9 illustrates a schematic perspective view and partial enlarged view of a triaxial mechanical arm 252 of a coiled catheter transferring mechanism 250 according to an embodiment.

In the embodiment provided with the buffer belt 230, the coiled catheter preparation unit may further include a coiled catheter transferring mechanism 250 for transferring the coiled catheter 14 on the buffer belt 230 to the coiled catheter pallet 100 in a predetermined posture. As shown in FIG. 9, in some embodiments, the coiled catheter transferring mechanism 250 may be a triaxial mechanical arm 252. Accordingly, the coiled catheter pallet 100 is supported on the circular belt and can move with the circular belt. After the triaxial mechanical arm 252 grabs the coiled catheter 14 from the buffer clamp 232, the coiled catheter 14 continues to maintain the vertical orientation, and by moving the coiled catheter 14 in the horizontal and vertical directions, the triaxial mechanical arm 252 can transfer the coiled catheter 14 to the coiled catheter pallet 100 when the coiled catheter pallet 100 supported on the catheter synchronous belt 120 is in the vertical state (for example, the coiled catheter pallet 100 in the vertical state as shown in FIG. 9), and the catheter tip portion 14a is accommodated in the catheter tip receiving portion 110.

In other embodiments, the coiled catheter transferring mechanism 250 may also be an industrial robot arm. The industrial robotic arm can grab the vertically oriented coiled catheter 14 from the buffer clamp 232, and then transfer the coiled catheter 14 to a coiled catheter pallet 100 oriented horizontally and make the catheter tip portion 14a be accommodated and supported in the catheter tip receiving portion 110.

In some embodiments, the coiled catheter preparation unit further includes a coiled catheter adjusting mechanism 260 configured to adjust the length of the catheter tip portion 14a of the coiled catheter 14 on the coiled catheter pallet 100 that extends beyond the catheter tip receiving portion 110 to a predetermined length.

Figure 10A:
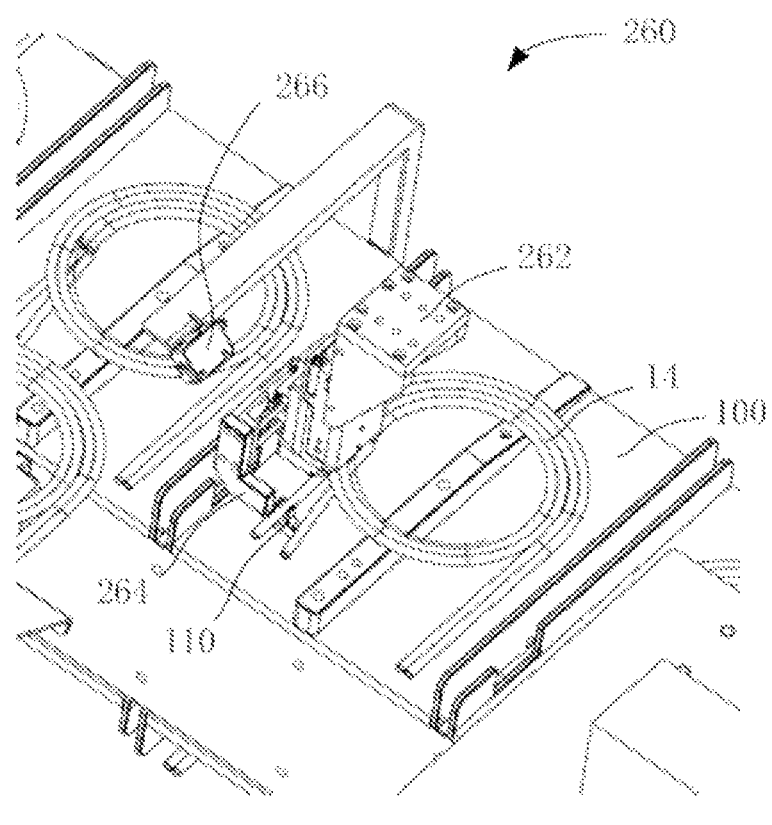
FIG. 10A illustrates a coiled catheter adjusting mechanism 260 according to an embodiment.
Figure 10B:
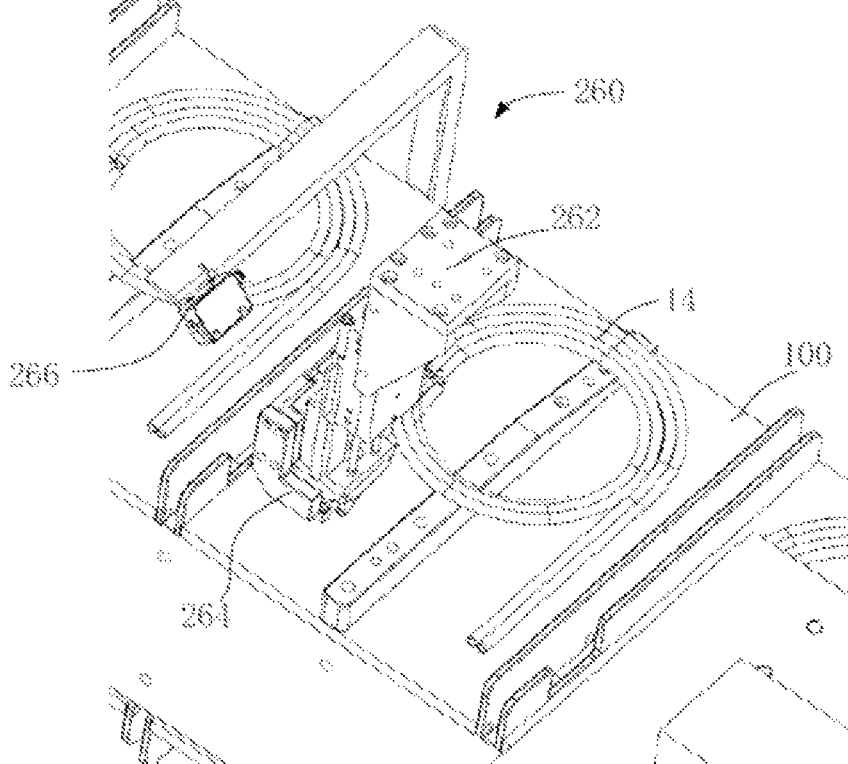
FIG. 10B illustrates a schematic perspective view of the coiled catheter adjusting mechanism 260 of FIG. 10A adjusting the catheter tip portion 14a according to an embodiment.

In some embodiments, as shown in FIG. 10A-10B, the coiled catheter adjusting mechanism 260 may include a catheter tip sensor 266. The catheter tip sensor 266 can emit a detection beam (for example, laser beam, infrared light beam) aiming at the catheter tip receiving portion 110 to detect whether the catheter tip receiving portion 110 receives the catheter tip portion 14a. If the catheter tip sensor 266 detects that the catheter tip portion 14a is received in the catheter tip receiving portion 110, the coiled catheter adjusting mechanism 260 performs a length-adjusting operation on the catheter tip portion 14a as described below. If it is detected that the catheter tip receiving portion 110 does not receive the catheter tip portion 14a, the system 1000 drives the coiled catheter synchronous belt 120 to transfer the next coiled catheter pallet 100 to the detection position of the catheter tip sensor 266 for detection.

Referring to FIG. 10A-10B, the coiled catheter adjusting mechanism 260 includes a coiled catheter vertical positioning device 262 and a coiled catheter push plate 264. The coiled catheter vertical positioning device 262 has a pressure block that can be driven (for example, by pneumatic, hydraulic or mechanical driving devices) to move vertically. When the pressure block is driven to move downward to abut against the top of the catheter tip receiving portion 110 (for example, the top of the protrusion 111), the pressure block will restrict the vertical movement of the catheter tip portion 14a received in the catheter tip receiving portion 110, so as to prevent the catheter tip portion from escaping from the groove during the adjusting process. Then, the coiled catheter push plate 264 is driven (for example, by pneumatic, hydraulic or mechanical driving device) to push the end of the catheter tip portion 14a that extends beyond the catheter tip receiving portion 110, so that the catheter tip portion 14a extends beyond the catheter tip receiving portion 110 to the predetermined length, as shown in FIG. 10B. However, the present disclosure is not limited thereto. The coiled catheter adjusting mechanism 260 may be any device or component that can adjust the length of the catheter tip portion 14a extending beyond the catheter tip receiving portion 110.

The specific structure of the coiled catheter preparation unit can be configured as required according to specific applications, which is not limited in this disclosure.

Figure 11:
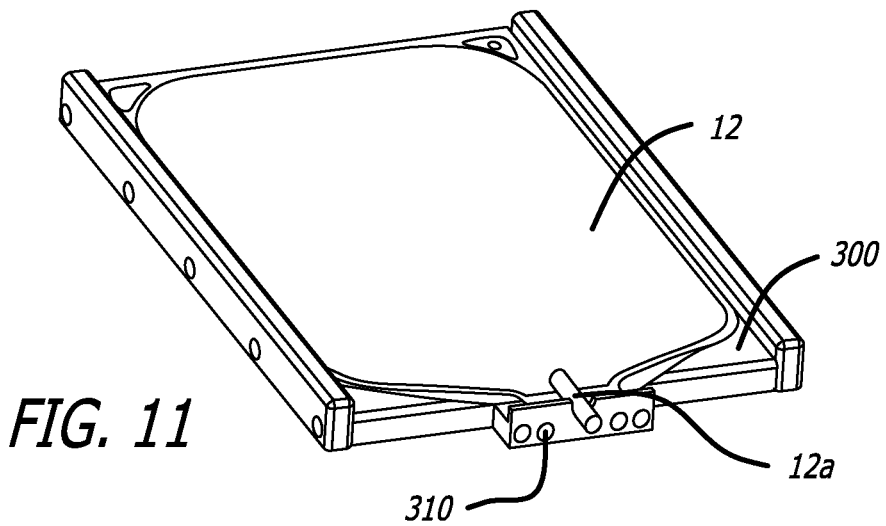
FIG. 11 illustrates a schematic perspective view of a container body pallet 300 according to an embodiment.

In some embodiments, the medical fluid container assembling system 1000 includes at least one container body pallet 300 for carrying the container body 12 thereon. Referring to FIG. 11, a container tube receiving portion 310 is provided at a substantially middle position of one side edge of the container body pallet 300 for receiving the container tube 12a of the container body 12. In the embodiment shown in FIG. 11, the container tube receiving portion 310 may be configured as a protrusion protruding from the bottom surface of the container body pallet 300, and a groove is provided on the protrusion, especially a groove with a semicircular bottom. The size of the groove is set to be equal to or slightly larger than the outer diameter of the container tube 12a, so as to receive the container tube 12a. The container tube receiving portion 310 is not limited to the structure shown in FIG. 11 and may be any specific form capable of receiving the container tube 12a.

Referring to FIGS. 2-3, in some embodiments, the medical fluid container assembling system 1000 further includes a plurality of container body pallets 300, and is provided with a container body synchronous belt 320 for conveying these container body pallets 300. The container body synchronous belt 320 is configured as a circular belt, and the plurality of container body pallets 300 can be carried thereon. The container body synchronous belt 320 can be driven (for example, by a stepping motor) to move these container body pallets 300 toward a container tube expander 500 (referring to FIG. 15 and FIG. 16).

As shown in FIGS. 2-3, in some embodiments, the medical fluid container assembling system 1000 further includes a container body preparation unit. Before assembling the container body 12 and the coiled catheter 14, the container body preparation unit performs a series of processing such as placing, adjusting, positioning on the container body 12, so that the container body 12 is placed on the container body pallets 300 in a predetermined posture, and the container tube 12a of the container body 12 protrudes from the container tube receiving portion 310 by a predetermined length.

Figure 12A:
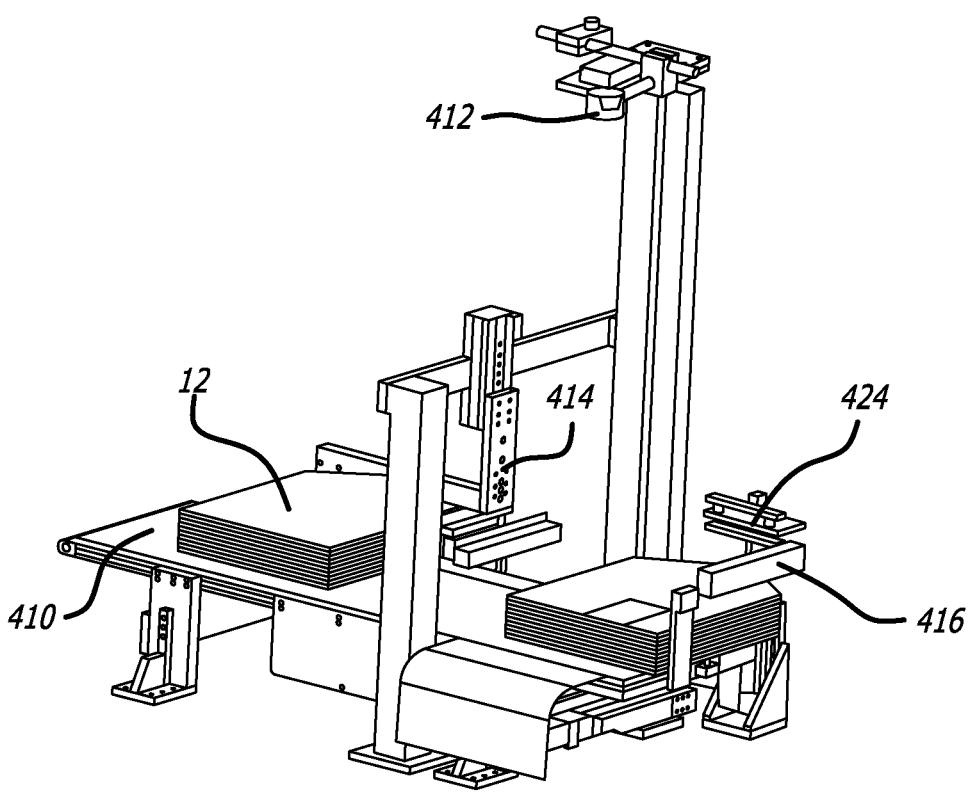
FIG. 12A illustrates a schematic perspective view of a feeding device of the container body 12 according to an embodiment.
Figure 12B:
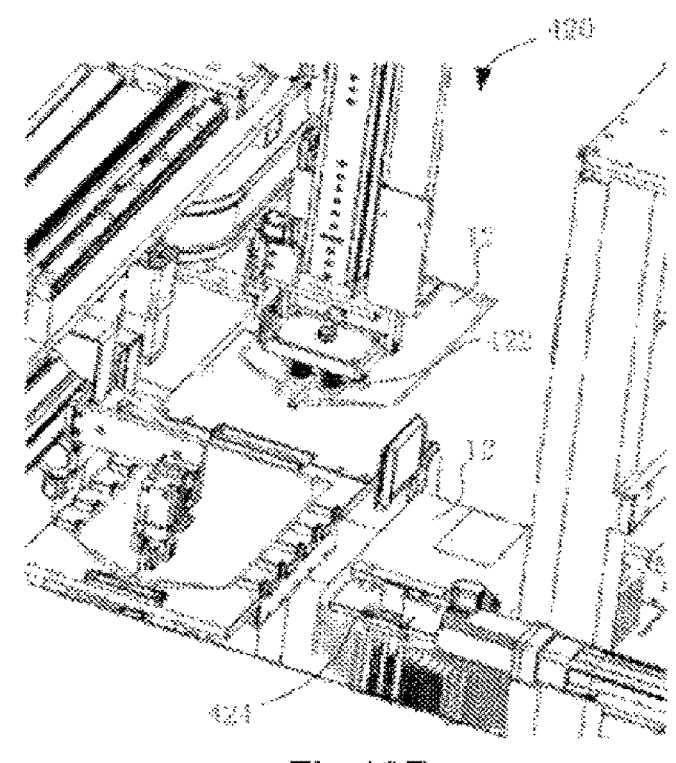
FIG. 12B illustrates a schematic perspective view of a container body gripper 420 according to an embodiment.

Referring to 12B, in some embodiments, the container body preparation unit may further include a container body gripper 420, which includes at least one sucker 422 and a container body indenter 424. When gripping the container body 12, the sucker 422 can suck the uppermost container body 12 in a group of stacked container bodies 12, while the container body indenter 424 presses the remaining container bodies 12 in the group of container bodies 12 to prevent the remaining container bodies 12 from moving. Referring to FIG. 12A, an operator may put several groups of stacked container bodies 12 (for example, a group of ten container bodies 12) on the feeding belt 410. Preferably, the container bodies 12 in a same group are placed partially overlapping each other, so that when the sucker 422 grasps the uppermost container body 12, the container body indenter 424 presses the remaining container bodies 12. The container body gripper 420 preferably has a plurality of suckers 422 to simultaneously suck a plurality of parts of the container body 12.

In some embodiments, referring to FIG. 12A, the feeding belt 410 may further include a visual detector 412, which is disposed above the gripping position. Before gripping the container body 12, the visual detector 412 is used to visually inspect the surface of the container body 12 to detect quality defects (for example, whether there are folded corners, or deformations) and/or placement defects (for example, front-back upside down, top-bottom upside down) of the container body 12. If determining that the container body 12 has quality or placement defects, the visual detector 412 generates a signal indicating the container body 12 is defective to trigger shutdown of the device and generate acoustic and/or visual alarms to alert an operator to deal with the defects.

In some embodiments, the visual detector 412 includes a camera device with image recognition function, which determines whether the container body 12 is placed in a way that meets the requirements by recognizing characters on the container body 12. In some embodiments, as shown in FIG. 12A, the visual detector 412 may further include light sources 414 and 416. The light sources 414 and 416 are disposed above the feeding belt 410, and are configured to emit a certain intensity of light to the surface of the container body 12 under test to supplement the light on the surface of the container body 12, so that the camera device can recognize the characters printed on the container body 12, thereby further improving the accuracy of visual inspection. As shown in FIG. 12A, the light source 414 is disposed above the conveying path of the container body 12. In order to prevent the feeding belt 410 from blocking the conveying of the container body 12 when the next group of container bodies 12 are transferred to the visual inspection position, the light source 414 may be configured to be liftable and lowerable in the vertical direction, so as to be lifted to avoid the container body 12 when the container body 12 is conveyed.

Figure 13:
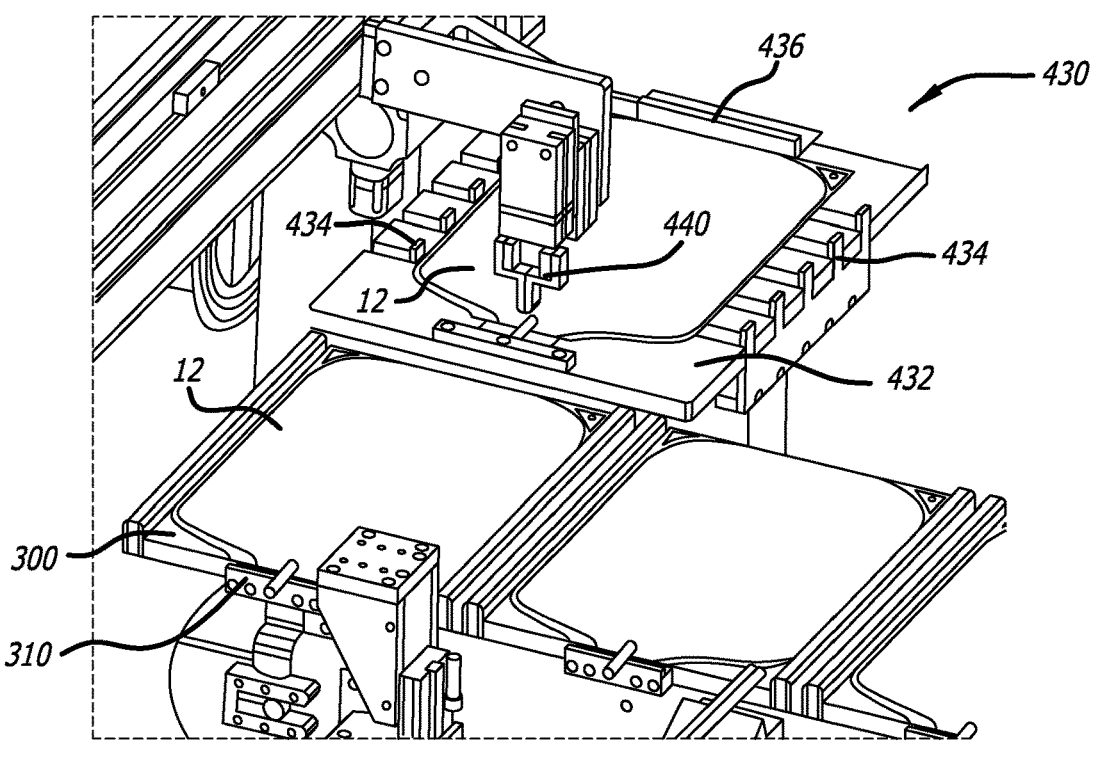
FIG. 13 illustrates a schematic perspective view of a container body positioning device 430 according to an embodiment.

In some embodiments, the container body preparation unit further includes a container body positioning device 430. Referring to FIG. 13, the container body positioning device 430 includes a plate 432, container body positioning blocks 434 disposed on two lateral sides of the plate 432, and a positioning bump 436.

The plate 432 is substantially rectangular, and the positioning bump 436 is fixedly disposed on the rear side edge of the plate 432 to limit the position of the container body 12 in the longitudinal direction. The container body positioning blocks 434 are configured as stoppers protruding upward from the plate 432. One or both of the two container body positioning blocks 434 can move relative to the plate 432. After the container body 12 is placed on the plate 432, the positioning bump 436 can limit the position of the container body 12 in the longitudinal direction (approximately along the up-down direction in FIG. 13) since it is fixed in position. The two container body positioning blocks 434 can move towards each other, so as to push the container body 12 to a predetermined position in the lateral direction (approximately along the left-right direction in FIG. 13). After the container body 12 is positioned at a predetermined position on the plate 432 by the body positioning blocks 434 and the positioning bump 436, a container tube clamp 440 can be used to clamp the container tube 12a of the container body 12 supported at the predetermined position on the plate 432, and to transfer the container body 12 to the container body pallet 300, so that the container tube receiving portion 310 receives the container tube 12a.

Since the container body 12 is located at a predetermined position on the plate 432 when the container tube clamp 440 clamps the container tube 12a, and the container body pallet 300 can be adjusted to a fixed position relative to the plate 432 in advance, it can be ensured that the container tube 12a protrudes from the container tube receiving portion 310 by a predetermined length after the container body 12 is transferred to the container body pallet 300.

Figure 14A:
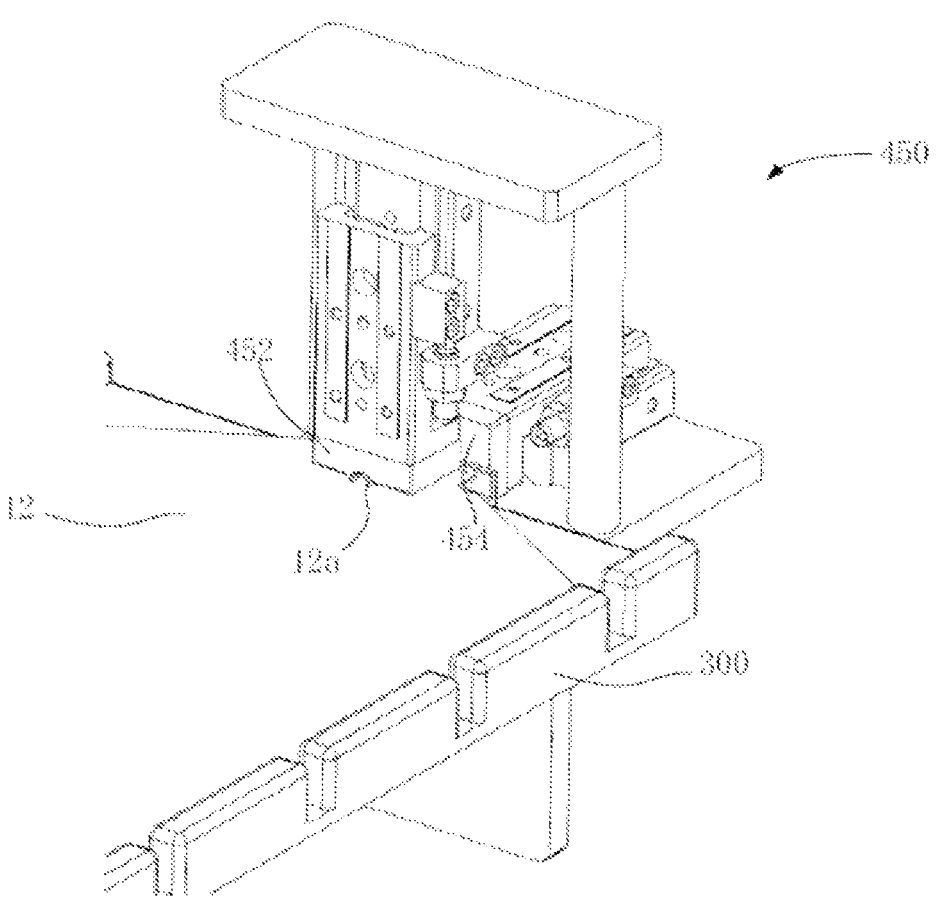
FIG. 14A illustrates a schematic perspective view of a container body adjusting mechanism 450 according to an embodiment.
Figure 14B:
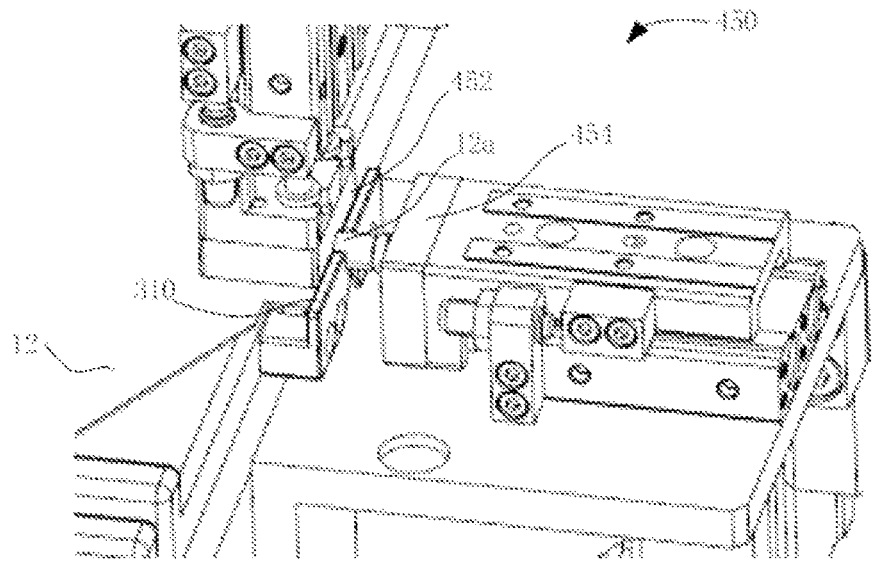

In some embodiments, in order to further ensure that the container tube 12a protrudes from the container tube receiving portion 310 by a predetermined length, the container body preparation unit may further include a container body adjusting mechanism 450. Referring to FIG. 14A, the container body adjusting mechanism 450 may include a container body vertical positioning device 452 and a container body push plate 454. The container body vertical positioning device 452 has a pressure block that can be driven (for example, by pneumatic, hydraulic or mechanical driving devices) to move vertically. When the pressure block is driven to move downward to abut against the top of the container tube receiving portion 310, the pressure block will restrict the container tube 12a received in the container tube receiving portion 310 from moving in the vertical direction, and accordingly prevent the container tube 12a from leaving the groove during the adjusting process. Then, referring to FIG. 14B, the container body push plate 454 is driven (for example, by pneumatic, hydraulic or mechanical driving device) to push an end of the container tube 12a extending beyond the container tube receiving portion 310, so that the container tube 12a extends beyond the container tube receiving portion 310 to a predetermined length. However, the present disclosure is not limited thereto. The container body adjusting mechanism 450 may be any device or component that can adjust the length of the container tube 12a extending beyond the container tube receiving portion 310.

The specific functional components of the container body preparation unit can be added or omitted as required according to specific applications, which is not limited in this disclosure.

Figure 15:
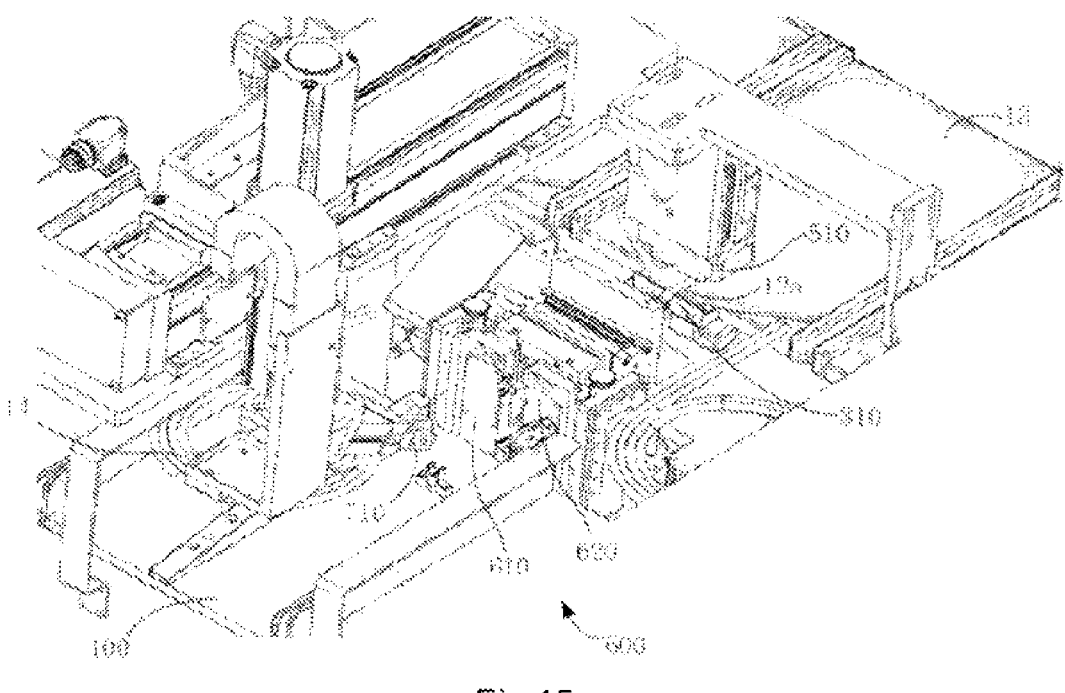
FIG. 15 illustrates a schematic perspective view of a container tube expander 500 and a catheter tip gluing device 600 according to an embodiment.
Figure 16:
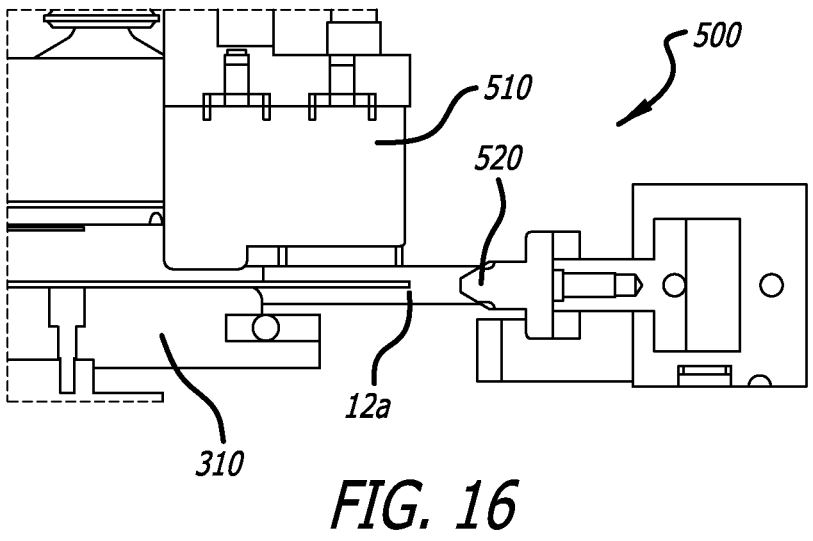

In some embodiments, the medical fluid container assembling system 1000 further includes a container tube expander 500, which is configured to perform a pre-assembly process on the adjusted container tube 12a to facilitate the assembly of the container body 12 and the catheter tip portion 14a. Referring to FIG. 15 and FIG. 16, a schematic perspective view of the container tube expander 500 is illustrated. The container tube expander 500 includes a container tube indenter 510 and an expansion head 520. As further shown in FIGS. 15-16, the container tube indenter 510 is provided with a concave portion with an arc-shaped cross-section, which can be driven to move toward or away from the container tube receiving portion 310. The container tube indenter 510 is configured to abut against the top of the container tube receiving portion 310, and when the container tube indenter 510 moves to a position where it abuts against the top of the container tube receiving portion 310, the concave portion of the container tube indenter 510 and the groove of the container tube receiving portion 310 cooperate to fix the container tube 12a relative to the container tube receiving portion 310, so as to prevent displacement of the container tube 12a during the process of inserting the expansion head 520 into the container tube 12a. Preferably, the part of the container tube indenter 510 that contacts the container tube 12a is made of polyurethane material, so as to minimize damage to the container tube 12a by the container tube indenter 510 when the container tube 12a is pressed.

Referring to FIG. 16, the head portion of the expansion head 520 is configured in a substantially conical shape, and its maximum outer diameter is slightly larger than the inner diameter of the container tube 12a. The surface of the head portion of the expansion head 520 can be smoothed, for example, applied with a Teflon coating. When the container tube indenter 510 secures the container tube 12a, the expansion head 520 can be driven so that the head portion of the expansion head 520 can be inserted into the container tube 12a to a certain depth, and thus at least a part of the container tube 12a is elastically expanded. In a period of time after the head portion of the expansion head 520 exits the container tube 12a(for example, 3 seconds), the elastically expanded container tube 12a can still maintain the expanded state to facilitate the insertion of the catheter tip portion 14a. It could be appreciated that the shape of the expansion head 520 is not limited to the illustrated embodiment, and any expansion head 520 with the function of expanding the diameter of the container tube can be used in the present disclosure.

Figure 17:
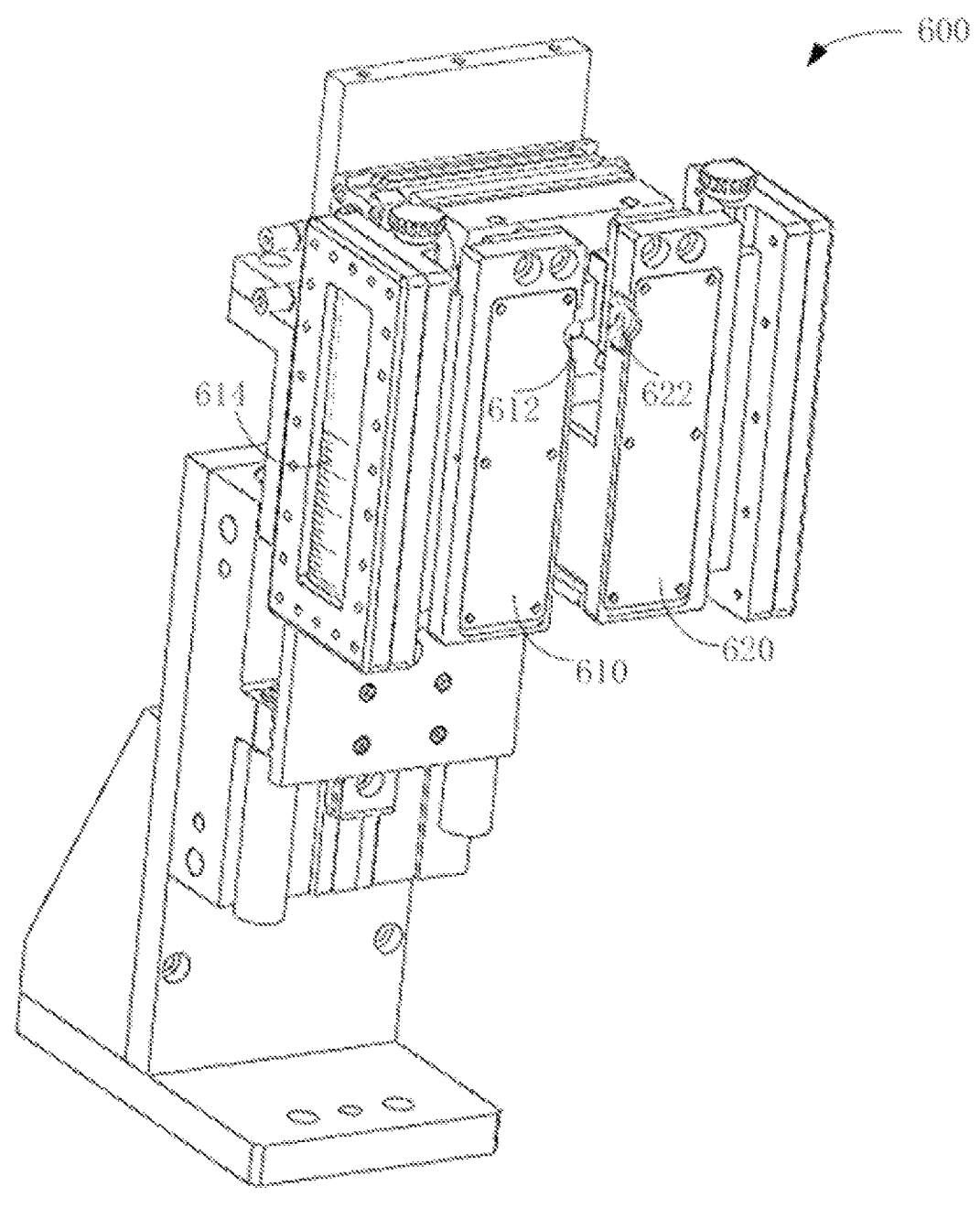
FIG. 17 illustrates a structural perspective view of the catheter tip gluing device 600 of FIG. 15.

In some embodiments, the medical fluid container assembling system 1000 further includes a catheter tip gluing device 600 configured to apply adhesive (for example, cyclohexanone) on a predetermined area of the catheter tip portion 14a. As shown in FIG. 17, the catheter tip gluing device 600 includes a first adhesive container 610 and a second adhesive container 620 that can be engaged with and separated from each other, each of which includes an adhesive storage cavity for storing adhesive. In some preferred embodiments, at least a portion of the first adhesive container 610 and/or the second adhesive container 620 is provided with a scale 614 indicating the remaining amount of adhesive (for example, the outer shell of the first adhesive container 610 and/or the second adhesive container 620 is made of a transparent material, and a scale is provided on the transparent material). In some embodiments, a fluid level sensor is disposed within the first adhesive container 610 and/or the second adhesive container 620 for indicating the remaining amount of adhesive, so as to measure the level of the adhesive.

The first adhesive container 610 and the second adhesive container 620 are respectively provided with outlet ports 612, 622 for contacting with the catheter tip portion 14a. Referring to FIG. 15, the catheter tip clamp 710 can be used to clamp the catheter tip portion 14a to move toward the catheter tip gluing device 600. When the catheter tip portion 14a moves to a position between the first adhesive container 610 and the second adhesive container 620, the first adhesive container 610 and the adhesive container 620 can be driven to move toward each other. When the first adhesive container 610 and the second adhesive container 620 are engaged with each other, the outlet ports 612 and 622 are in contact with the catheter tip portion 14a and surround the catheter tip portion 14a, thereby applying the adhesive in the first adhesive container 610 and the second adhesive container 620 on a predetermined area of the catheter tip portion 14a. It could be appreciated that the number of the adhesive containers and the outlets ports provided on the catheter tip gluing device 600 of the present disclosure is not limited to two, three, four or more adhesive containers and outlet ports can also be provided.

In some embodiments, the predetermined area where the adhesive is applied onto the catheter tip portion 14a may start from the end edge of the catheter tip portion 14a. In some embodiments, the predetermined area where the adhesive is applied may start at a distance from the end edge of the catheter tip portion 14a, for example, 0.5-1 mm from the end edge of the catheter tip portion 14a. The width of the predetermined area where the adhesive is applied may be 2-5 mm The medical fluid container system assembling system 1000 further includes an assembling mechanism configured to align the catheter tip portion 14a applied with adhesive with the expanded container tube 12a, and insert the catheter tip portion 14a into the container tube 12a to a predetermined depth.

Figure 18:
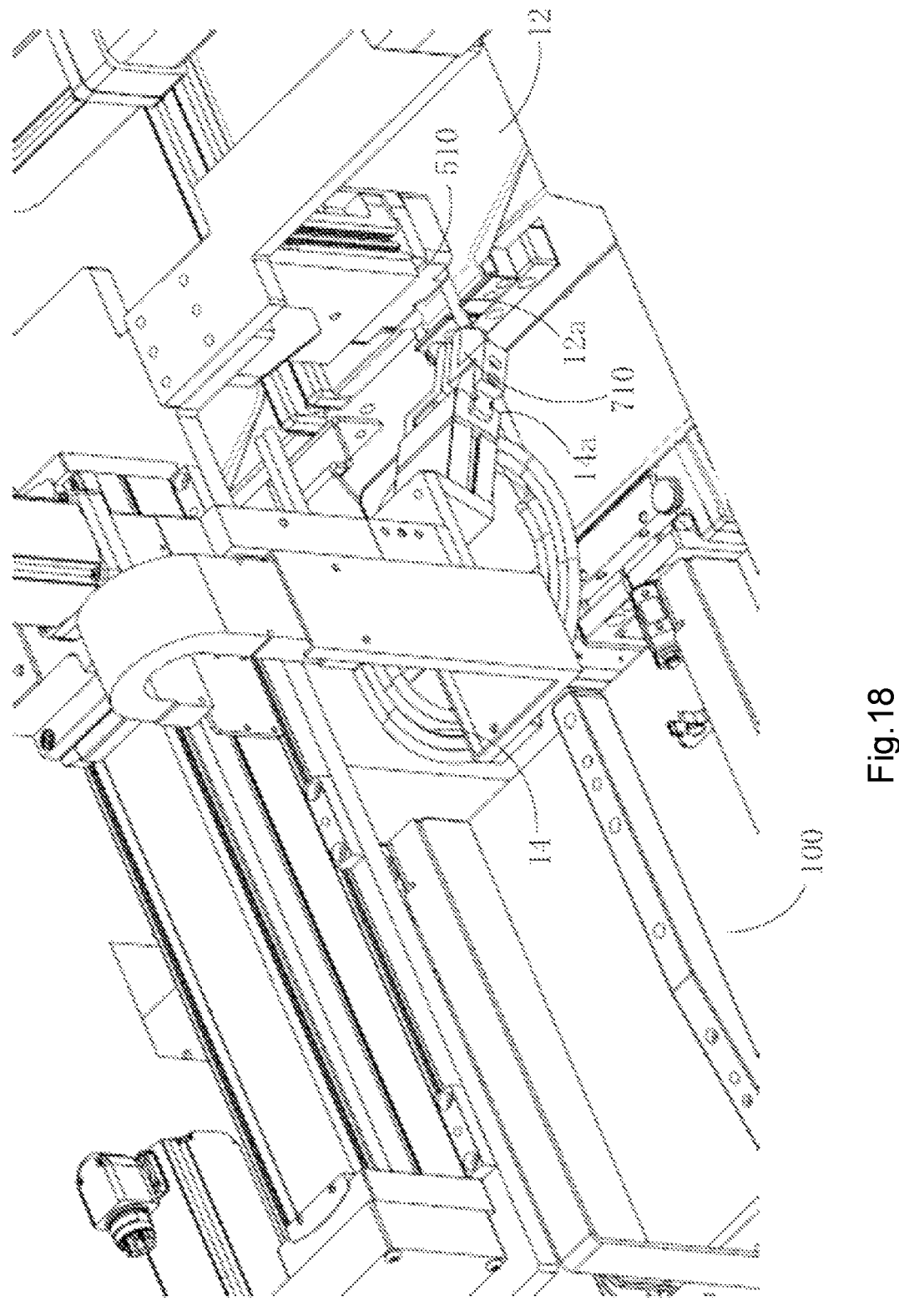
FIG. 18 illustrates a schematic perspective view of the assembling mechanism according to an embodiment.

Referring to FIG. 18, the assembling mechanism includes a catheter tip clamp 710, which is used to clamp the catheter tip portion 14a at a predetermined position. For example, the catheter tip clamp 710 can approach the catheter tip portion 14a and clamp the catheter tip portion 14a through the sidewall gaps 130, 130' of the coiled catheter pallets 100, 100', so that the catheter tip portion 14a exceeds the length of the catheter tip clamp 710, which is convenient for subsequent gluing process and insertion of the container tube 12a.

While the expansion head 520 expands the container tube 12a, the catheter tip clamp 710 clamps the catheter tip portion 14a and sends it to the gluing device 600 for gluing operation. After the container tube 12a is expanded, the expansion head 520 and the gluing device 600 are moved downwards, and at the same time, the catheter tip clamp 710 clamps the catheter tip portion 14a and moves toward the container tube 12a, so that the catheter tip portion 14a is aligned with the container tube 12a. During this process, the container tube indenter 510 still abuts against the container to fix the container tube 12a.

Then, the assembly mechanism controls the catheter tip clamp 710 to clamp the adhesive-coated catheter tip portion 14a and insert it into the container tube 12a (the insertion depth can be greater than or equal to 6 mm, and less than or equal to 15 mm, for example, 10 mm), thereby completing the container body 12 intubation assembly. The insertion action is completed while the container tube 12a is still elastically expanded.

In some embodiments, an assembly quality inspection mechanism capable of visually inspecting the assembled medical fluid container 10 may be optionally provided above the assembly position to automatically detect the quality of the assembly. The assembly quality inspection mechanism includes a camera device with an image recognition function to perform image recognition on the insertion depth and the twist degree of the assembled catheter tip portion 14a and the container tube 12a to determine whether the catheter tip portion 14a and the container tube 12a are properly assembled. If the assembly is determined to be poor, the corresponding medical fluid container 10 is scrapped. In some embodiments, a container body waste bin may also be provided to collect the scrapped medical fluid containers 10.

Hereinafter, a method of assembling a medical fluid container according to the present disclosure will be described with reference to the accompanying drawings. Referring to FIG. 19, a schematic flowchart of a method 2000 for assembling a medical fluid container is provided according to an embodiment of the present disclosure.

In block 2100, the medical fluid container assembling system 1000 supports the welded coiled catheter 14 on the coiled catheter pallet 100, wherein the catheter tip portion 14a of the coiled catheter 14 is received in the catheter tip receiving portion 110 on the coiled catheter pallet 100.

In block 2200, the coiled catheter 14 is placed on the coiled catheter pallet 100 in a predetermined posture by the coiled catheter preparation unit, and the catheter tip portion 14a of the coiled catheter 14 extends a predetermined length beyond the catheter tip receiving portion 110.

In block 2300, the container body 12 is supported on the container body pallet 300, wherein the container tube 12a of the container body 12 is received in the container tube receiving portion 310 on the container body pallet 300.

In block 2400, the container body 12 is placed on the container body pallet 300 in a predetermined posture by the container body preparation unit, and the container tube 12a of the container body 12 extends a predetermined length beyond the container tube receiving portion 310.

In block 2500, the container tube expander 500 is used to expand at least a portion of the container tube 12a, and the catheter tip gluing device 600 is used to apply an adhesive on a predetermined area of the catheter tip portion 14a.

In block 2600, the assembly mechanism is used to align the adhesive-coated catheter tip portion 14a with the at least partially expanded container tube 12a and insert the catheter tip portion 14a into the container tube 12a to a predetermined depth.

In some embodiments, block 2200 of the method 2000 of the present disclosure further includes: adjusting, by the coiled catheter adjusting mechanism 260, the length of the catheter tip portion 14a of the coiled catheter 14 supported on the coiled catheter pallet 100 out of the catheter tip receiving portion 110 to the predetermined length.

In some embodiments, optionally, the method 2000 of the present disclosure further includes: before block 2100, using the coiled catheter gripping mechanism 210 to grip the welded coiled catheter 14.

In some embodiments, before block 2100, and after the coiled catheter gripping mechanism 210 grips the coiled catheter 14, the coiled catheter gripping mechanism 210 is used to make the gripped coiled catheter 14 pass through the coiled catheter detector 220 in a horizontal posture, and the coiled catheter detector 220 is used to detect whether the height of the coiled catheter 14 passing through the coiled catheter detector 220 in the vertical direction exceeds a predetermined range.

In some embodiments, before block 2100, and after the coiled catheter gripping mechanism 210 grips the coiled catheter 14 (preferably, after the coiled catheter detector 220 detects the welding quality of the coiled catheter 14), at least one coiled catheter 14 gripped by the coiled catheter gripping mechanism 210 is received on a buffer belt 230 disposed upstream of the coiled catheter pallet 100, and the buffer belt 230 is used to transfer the coiled catheter 14 toward the coiled catheter pallet 100.

In some embodiments, before block 2100 and after the buffer belt 230 receives the coiled catheter 14, the coiled catheter transfer mechanism 250 is used to transfer the coiled catheter 14 supported on the buffer belt 230 to the coiled catheter pallet 100 in a predetermined posture.

In some embodiments, block 2400 of the method 2000 of the present disclosure may further optionally include: using the container body adjusting mechanism 450 to adjust a length of the container tube 12a of the container body 12 supported on the container body pallet 300 that extends beyond the container tube receiving portion 310 to a predetermined length.

In some embodiments, before block 2300, at least one sucker 422 is used to grasp the uppermost container body 12 in a group of container bodies, while the container body indenter 424 is used to press the remaining container bodies 12 in the group of container bodies.

In some embodiments, before block 2300, and after the container body gripper 420 grips the container body 12, the container body 12 is pressed against the positioning bump 436, the container body positioning block 434 is moved relative to the plate 432, and thus, the container body 12 supported on the container body positioning device 430 is pushed to a predetermined position on the plate 432.

In some embodiments, before block 2300, after pushing the container body 12 to a predetermined position on the plate 432, the container tube clamp 440 is used to clamp the container body 12 supported at the predetermined position on the plate 432 of the container body positioning device 430 and transfer the container body 12 to the container body pallet 300.

In some embodiments, block 2500 of the method 2000 of the present disclosure further includes: abutting the container tube indenter 510 against the top of the container tube receiving portion 310, and while the container tube indenter 510 abuts against the container tube 12a, inserting the expansion head 520 at least partially into the container tube 12a.

In some embodiments, after block 2600, an assembly quality inspection mechanism is optionally used to visually inspect the assembled medical fluid container 10.

Those skilled in the art can foresee that the blocks described above can be adjusted according to actual conditions, such as adjusting the order of the blocks, or omitting some blocks.

The embodiments of the present disclosure described above in conjunction with the accompanying drawings are only schematic. For example, the division of the units can be regarded as only a functional division, and there may be other divisions in actual implementation, for example, multiple units or components may be divided. It can be combined or integrated into another system, or some units or components can be omitted. On the other hand, the displayed or discussed mutual coupling or communication connection may be indirect coupling or indirect communication connection through some interfaces, devices or units. In addition, for the method embodiments described in the embodiments herein, the present invention is not limited by the described sequence of actions, because according to the present invention, certain steps can be performed in other sequences or simultaneously.

Although the present application has been described in detail with reference to certain preferred embodiments, there are various changes and modifications within the scope and spirit of one or more independent aspects of the described application.

What is claimed is:

1. A medical fluid container assembling system comprising:

at least one coiled catheter pallet for supporting a coiled catheter, the coiled catheter pallet being provided with a catheter tip receiving portion for receiving a catheter tip portion of the coiled catheter;

a coiled catheter preparation unit configured to place the coiled catheter on the coiled catheter pallet in a predetermined posture, and cause the catheter tip portion of the coiled catheter to extend a predetermined length beyond the catheter tip receiving portion;

at least one container body pallet for supporting a container body, the container body pallet being provided with a container tube receiving portion for receiving a container tube of a container body;

a container body preparation unit configured to place the container body on the container body pallet in a predetermined posture, and cause the container tube of the container body to extend a predetermined length beyond the container tube receiving portion;

a container tube expander configured to expand at least a portion of the container tube;

a catheter tip gluing device configured to apply adhesive on a predetermined area of the catheter tip portion; and an assembling mechanism configured to align the catheter tip portion applied with adhesive with an at least partially expanded container tube, and insert the catheter tip portion into the container tube to a predetermined depth.

2. The system of claim 1, wherein the coiled catheter preparation unit comprises a coiled catheter adjusting mechanism configured to adjust the length of the catheter tip portion of the coiled catheter on the coiled catheter pallet that extends beyond the catheter tip receiving portion to a predetermined length.

3. The system of claim 2, wherein the coiled catheter preparation unit further comprises a coiled catheter gripping mechanism for gripping a welded coiled catheter.

4. The system of claim 3, wherein the coiled catheter gripping mechanism comprises a first gripper for gripping the catheter tip portion of the coiled catheter and at least three second grippers for gripping an inner circumference of the coiled catheter, and gripping portions of the second grippers are arranged in the same horizontal plane.

5. The system of claim 4, wherein the coiled catheter preparation unit further comprises a coiled catheter detector, wherein the coiled catheter gripping mechanism is configured to cause the gripped coiled catheter to pass by the coiled catheter detector in a substantially horizontal orientation, and wherein the coiled catheter detector is configured to inspect whether the height of the coiled catheter passing by the coiled catheter detector exceeds a predetermined range.

6. The system of claim 5, wherein the coiled catheter detector comprises a laser sensor disposed at a height lower than the plane where the gripping portion of the second grippers locates by a predetermined distance.

7. The system of claim 3, wherein the coiled catheter preparation unit further comprises a buffer belt disposed upstream of the coiled catheter pallet, and wherein the buffer belt is configured as a circular belt for receiving at least one coiled catheter from the coiled catheter gripping mechanism and delivering the coiled catheter to the coiled catheter pallet.

8. The system of claim 7, wherein the coiled catheter preparation unit further comprises a coiled catheter transferring mechanism for transferring the coiled catheter on the buffer belt to the coiled catheter pallet in a predetermined posture.

9. The system of claim 8, wherein the coiled catheter transferring mechanism is an industrial robot or a triaxial mechanical arm.

10. The system of claim 1, wherein the at least one coiled catheter pallet is supported on a coiled catheter synchronous belt configured for moving the at least one coiled catheter pallet supported thereon toward the catheter tip gluing device.

11. The system of claim 1, wherein the at least one container body pallet is supported on a container body synchronous belt configured for moving the at least one container body pallet supported thereon toward the container tube expander.

12. The system of claim 1, wherein the container body preparation unit comprises a container body adjusting mechanism configured to adjust the length of the container tube of the container body on the container body pallet that extends beyond the container tube receiving portion to a predetermined length.

13. The system of claim 1, wherein the container body preparation unit further comprises a container body gripper comprising at least one sucker for sucking a topmost one of a set of container bodies, and a container body indenter for pressing other container bodies of the set of container bodies.

14. The system of claim 1, wherein the container body preparation unit further comprises a container body positioning device comprising a plate and a container body positioning block disposed on the plate, and the container body positioning block is configured to be movable on the plate so as to push the container body supported on the container body positioning block to a predetermined position on the plate.

15. The system of claim 14, wherein the container body preparation unit further comprises a container tube clamp configured to clamp the container tube of the container body supported at the predetermined position on the plate of the container body positioning device, and transfer the container body to the container body pallet.

16. The system of claim 1, wherein the container tube expander comprises a substantially conical expansion head and a container tube indenter, the container tube indenter is configured to abut against a top of the container tube receiving portion, and the expansion head is configured to allow the expansion head to be at least partially inserted into the container tube while the container tube indenter is abutting against the top of the container tube receiving portion.

17. The system of claim 1, wherein the catheter tip gluing device comprises a first adhesive container and a second adhesive container that can be engaged with and separated from each other, wherein the first adhesive container and the second adhesive container are respectively provided with outlet ports for contacting with the catheter tip portion, and wherein when the first adhesive container and the second adhesive container are engaged with each other, their outlet ports contact with the catheter tip portion, so that adhesive in the first adhesive container and the second adhesive container is applied on the predetermined area of the catheter tip portion.

18. The system of claim 17, wherein at least a portion of the first adhesive container and/or the second adhesive container is made of transparent material and is provided with a scale indicating a remaining amount of adhesive; or the first adhesive container and/or the second adhesive container is provided with a fluid level sensor therein for indicating the remaining amount of adhesive.

19. The system of claim 1, further comprising:

an inspection mechanism configured to visually inspecting the assembled medical fluid container.

20. A method for assembling a medical fluid container, the method comprising:

supporting a welded coiled catheter on a coiled catheter pallet, a catheter tip portion of the coiled catheter being received in a catheter tip portion receiving portion of the coiled catheter pallet;

placing, by a coiled catheter preparation unit, the coiled catheter on the coiled catheter pallet in a predetermined posture, and causing the catheter tip portion of the coiled catheter to extend a predetermined length beyond the catheter tip portion receiving portion;

supporting a container body on a container body pallet, a container tube of the container body being received in a container tube receiving portion of the container body pallet;

placing, by a container body preparation unit, the container body on the container body pallet in a predetermined posture, and causing the container tube of the container body to extend a predetermined length beyond the container tube receiving portion;

expanding, by a container tube expander, at least a portion of the container tube;

applying, by a catheter tip gluing device, adhesive on a predetermined area of the catheter tip portion; and aligning, by an assembling mechanism, the catheter tip portion applied with adhesive with at least partially expanded container tube, and inserting the catheter tip portion into the container tube to a predetermined depth.

21. The method of claim 20, wherein the coiled catheter preparation unit further comprises a coiled catheter adjusting mechanism, and the method further comprises:

adjusting, by the coiled catheter adjusting mechanism, the length of the catheter tip portion of the coiled catheter on the coiled catheter pallet that extends beyond the catheter tip receiving portion to a predetermined length.

22. The method of claim 21, wherein the coiled catheter preparation unit further comprises a coiled catheter gripping mechanism, and the method further comprises:

gripping, by the coiled catheter gripping mechanism, the welded coiled catheter before the welded coiled catheter being supported on the coiled catheter pallet.

23. The method of claim 22, wherein the coiled catheter preparation unit further comprises a coiled catheter detector, and the method further comprises:

after gripping the coiled catheter by the coiled catheter gripping mechanism, causing the gripped coiled catheter in a substantially horizontal orientation to pass by the coiled catheter detector, and inspecting, by the coiled catheter detector, whether the height of the coiled catheter passing by the coiled catheter detector in a vertical direction exceeds a predetermined range.

24. The method of claim 22, further comprising:

after the coiled catheter gripping mechanism grips the coiled catheter, causing at least one gripped coiled catheter from the coiled catheter gripping mechanism to be received by a buffer belt disposed upstream of the coiled catheter pallet, and delivering the coiled catheter to the coiled catheter pallet by the buffer belt.

25. The method of claim 24, further comprising:

transferring, by a coiled catheter transferring mechanism, the coiled catheter received on the buffer belt to the coiled catheter pallet in a predetermined posture.

26. The method of claim 20, wherein the container body preparation unit further comprises a container body adjusting mechanism, and the method further comprises:

adjusting, by the container body adjusting mechanism, the length of the container tube of the container body supported on the container body pallet that extends beyond the container tube receiving portion to a predetermined length.

27. The method of claim 20, wherein the container body preparation unit further comprises a container body gripper which comprises at least one sucker and a container body indenter, and the method further comprises:

gripping, before adjusting the length of the container tube of the container body with the container body adjusting mechanism, the topmost one of a set of container bodies with the at least one sucker, while pressing the other container bodies of the set of container bodies with the container body indenter.

28. The method of claim 20, wherein the container body preparation unit further comprises a container body positioning device that comprises a plate and a container body positioning block disposed on the plate, wherein the container body positioning block is configured to be movable relative to the plate, enabling the container body supported on the container body positioning device to be pushed to a predetermined position on the plate; and the method further comprises:

moving, before placing the container body on the container body pallet in a predetermined posture, the container body positioning block relative to the plate, thereby pushing the container body supported on the container body positioning device to a predetermined position on the plate.

29. The method of claim 28, wherein the container body preparation unit further comprises a container tube clamp, and the method further comprises:

clamping, by the container tube clamp, the container tube of the container body in a predetermined position on the plate of the container body positioning device; and transferring the container body to the container body pallet.

30. The method of claim 20, wherein the container tube expander comprises a substantially conical expansion head and a container tube indenter, wherein the container tube indenter is configured to abut against the top of the container tube receiving portion, and wherein the expansion head is configured to allow the expansion head to be at least partially inserted into the container tube while the container tube indenter is abutting against the top of the container tube receiving portion; and the method further comprises:

causing the container tube indenter to abut against the top of the container tube receiving portion; and inserting the expansion head into the container tube while the container tube indenter is abutting against the top of the container tube receiving portion.

31. The method of claim 20, wherein the method further comprises:

visually inspecting, by an inspection mechanism, an assembly of the medical fluid container and the coil catheter.

\* \* \* \* \*